US010863915B2

(12) United States Patent
Stewart et al.

(10) Patent No.: US 10,863,915 B2
(45) Date of Patent: Dec. 15, 2020

(54) ANNOTATION HISTOGRAM

(71) Applicant: Boston Scientific Scimed Inc., Maple Grove, MN (US)

(72) Inventors: Brian Stewart, North Reading, MA (US); Vasiliy E. Buharin, Arlington, MA (US); Mordechai Perlman, Cambridge, MA (US); Nathan H. Bennett, Cambridge, MA (US)

(73) Assignee: Boston Scientific Scimed Inc, Maple Grove, MN (US)

( * ) Notice: Subject to any disclaimer, the term of this patent is extended or adjusted under 35 U.S.C. 154(b) by 142 days.

(21) Appl. No.: 15/955,505

(22) Filed: Apr. 17, 2018

(65) Prior Publication Data
US 2018/0296108 A1    Oct. 18, 2018

Related U.S. Application Data

(60) Provisional application No. 62/486,920, filed on Apr. 18, 2017.

(51) Int. Cl.
*A61B 5/044*    (2006.01)
*G06T 11/20*    (2006.01)
(Continued)

(52) U.S. Cl.
CPC ............ *A61B 5/044* (2013.01); *A61B 5/0245* (2013.01); *A61B 5/0402* (2013.01); *A61B 5/0452* (2013.01); *A61B 5/743* (2013.01); *A61B 34/20* (2016.02); *A61B 34/25* (2016.02); *G06F 3/04842* (2013.01); *G06F 40/169* (2020.01);
(Continued)

(58) Field of Classification Search
CPC ......... A61B 5/044; A61B 34/20; A61B 34/25; A61B 5/0245; A61B 5/0404; A61B 5/0452; A61B 5/0422; G06F 40/169; G06F 3/04842; G06T 11/206
See application file for complete search history.

(56) References Cited

U.S. PATENT DOCUMENTS 4,721,114 A    1/1988    DuFault et al.
5,058,599 A    10/1991    Andersen
(Continued)

FOREIGN PATENT DOCUMENTS

WO    2013123549 A1    8/2013

OTHER PUBLICATIONS

Anonymous: "Advanced Mapping and Navigation Modalities—Clinical Gate", Oct. 30, 2016, Retrieved from the Internet: https://clinicalgate.com/advanced-mapping-and-navigation-modalities/ Retrieved on Jun. 26, 2018.
(Continued)

*Primary Examiner* — Tadesse Hailu
(74) *Attorney, Agent, or Firm* — Faegre Drinker Biddle & Reath LLP

(57) ABSTRACT

Systems and methods for facilitating processing of cardiac information based on sensed electrical signals include a processing unit configured to receive a set of electrical signals; receive an indication of a measurement location corresponding to each electrical signal of the set of electrical signals; and generate, based on at least one of an annotation waveform corresponding to each electrical signal of the set of electrical signals and a set of annotation mapping values, an annotation histogram.

20 Claims, 13 Drawing Sheets

(51) Int. Cl.
*G06F 17/24* (2006.01)
*G06F 3/0484* (2013.01)
*A61B 34/20* (2016.01)
*A61B 5/00* (2006.01)
*A61B 5/0452* (2006.01)
*A61B 5/0245* (2006.01)
*A61B 34/00* (2016.01)
*A61B 5/0402* (2006.01)
*G06F 40/169* (2020.01)
*A61B 18/14* (2006.01)
*A61B 18/00* (2006.01)
*A61B 5/06* (2006.01)
*A61B 5/042* (2006.01)

(52) U.S. Cl.
CPC .......... *G06T 11/206* (2013.01); *A61B 5/0422* (2013.01); *A61B 5/0538* (2013.01); *A61B 5/063* (2013.01); *A61B 5/6852* (2013.01); *A61B 5/7221* (2013.01); *A61B 18/1492* (2013.01); *A61B 2018/00351* (2013.01); *A61B 2018/00577* (2013.01); *A61B 2018/00839* (2013.01); *A61B 2018/00875* (2013.01); *A61B 2034/2051* (2016.02); *A61B 2562/04* (2013.01); *A61B 2562/06* (2013.01); *G06T 2200/24* (2013.01)

(56) References Cited

U.S. PATENT DOCUMENTS

| | | | |
|---|---|---|---|
| 6,070,094 A | 5/2000 | Swanson et al. | |
| 6,233,491 B1 | 5/2001 | Kordis et al. | |
| 6,236,883 B1 | 5/2001 | Ciaccio et al. | |
| 6,735,465 B2 | 5/2004 | Panescu | |
| 7,515,954 B2 | 4/2009 | Harlev et al. | |
| 8,103,338 B2 | 1/2012 | Harlev et al. | |
| 8,229,545 B2 | 7/2012 | Afonso | |
| 8,428,700 B2 | 4/2013 | Harlev et al. | |
| 8,615,287 B2 | 12/2013 | Harlev et al. | |
| 8,647,284 B2 | 2/2014 | Afonso | |
| 8,838,216 B2 | 9/2014 | Francis et al. | |
| 8,948,837 B2 | 2/2015 | Harlev et al. | |
| 9,078,573 B2 | 7/2015 | Ramanathan et al. | |
| 9,265,951 B2 | 2/2016 | Sweeney | |
| 2007/0177801 A1* | 8/2007 | Kawamoto | G06F 3/04883 382/187 |
| 2009/0069704 A1* | 3/2009 | MacAdam | A61B 5/044 600/523 |
| 2011/0206256 A1 | 8/2011 | Ramanathan et al. | |
| 2014/0005563 A1 | 1/2014 | Ramanathan et al. | |
| 2015/0065836 A1 | 3/2015 | Thakur et al. | |
| 2015/0208938 A1* | 7/2015 | Houben | A61B 5/7203 600/509 |
| 2015/0216438 A1 | 8/2015 | Bokan et al. | |
| 2015/0366476 A1 | 12/2015 | Laughner et al. | |
| 2017/0079539 A1* | 3/2017 | Chauhan | A61B 5/04012 |
| 2017/0156616 A1* | 6/2017 | Talkachova | A61B 5/04012 |
| 2017/0224238 A1* | 8/2017 | Arunachalam | A61B 5/046 |
| 2018/0296113 A1 | 10/2018 | Stewart et al. | |
| 2018/0296167 A1 | 10/2018 | Stewart et al. | |

OTHER PUBLICATIONS

International Search Report and Written Opinion issued in PCT/US2018/027909, dated Jun. 28, 2018, 10 pages.

International Search Report and Written Opinion issued in PCT/US2018/027927, dated Jul. 16, 2018, 15 pages.

Przemyslaw Zajac et al., "EJMT 4(13) 2016©BULLET European Journal of Medical Technologies Corresponding address: Electroanatomic Mapping System—the useful tool for electrophysilogy", Dec. 31, 2016.

International Preliminary Report on Patentability issued in PCT/US2018/027909, dated Oct. 31, 2019, 7 pages.

International Preliminary Report on Patentability issued in PCT/US2018/027927, dated Oct. 31, 2019, 9 pages.

* cited by examiner

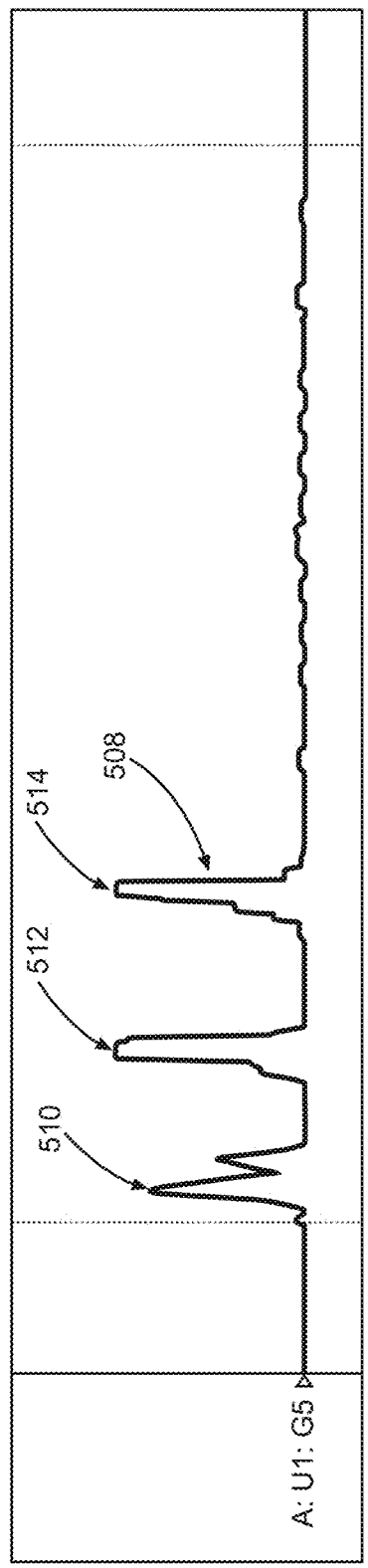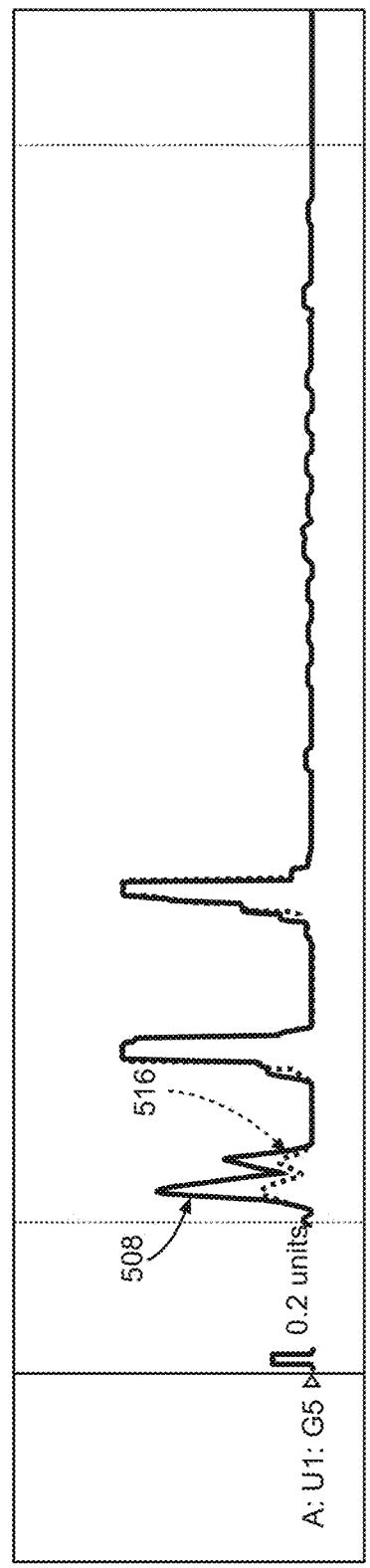

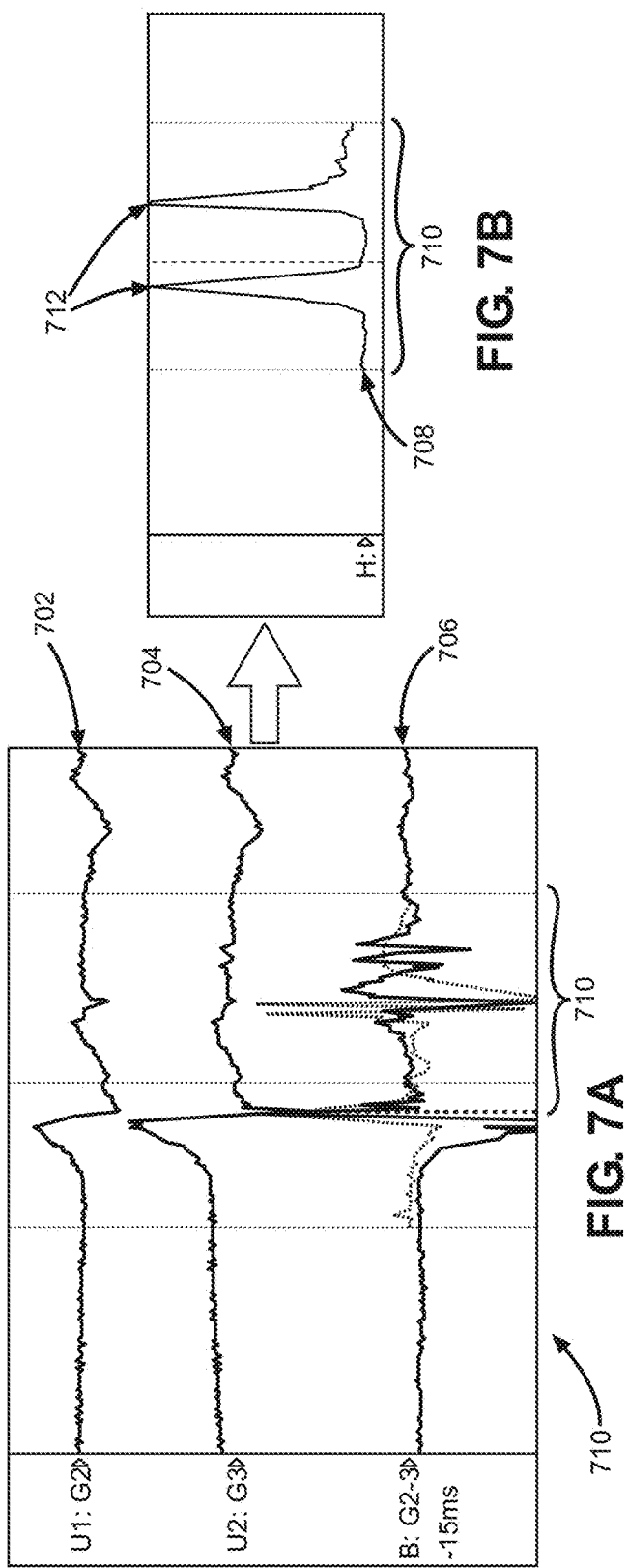
FIG. 7A
FIG. 7B
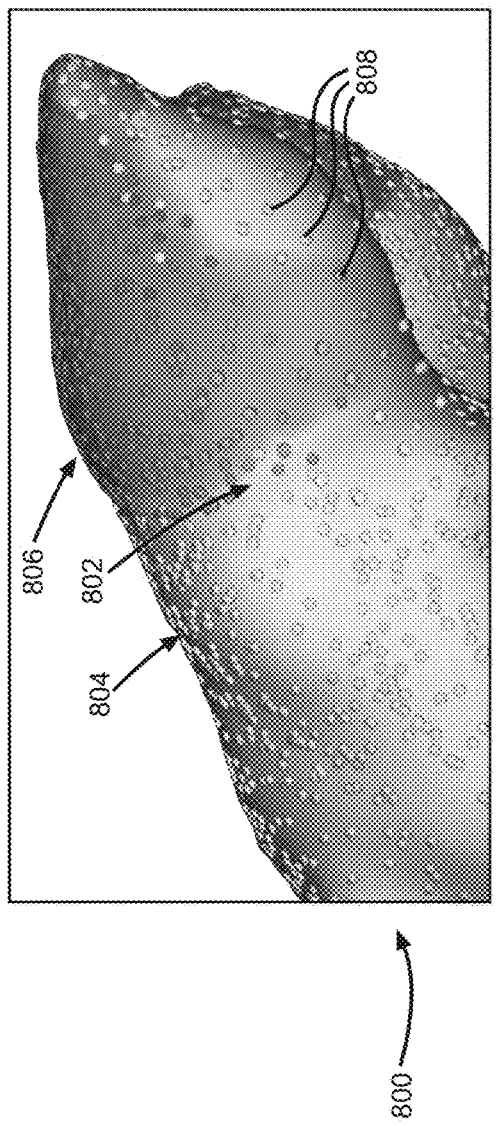
FIG. 8

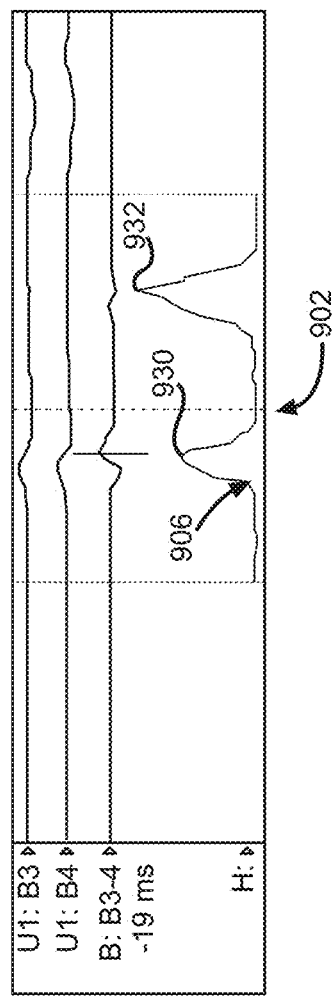
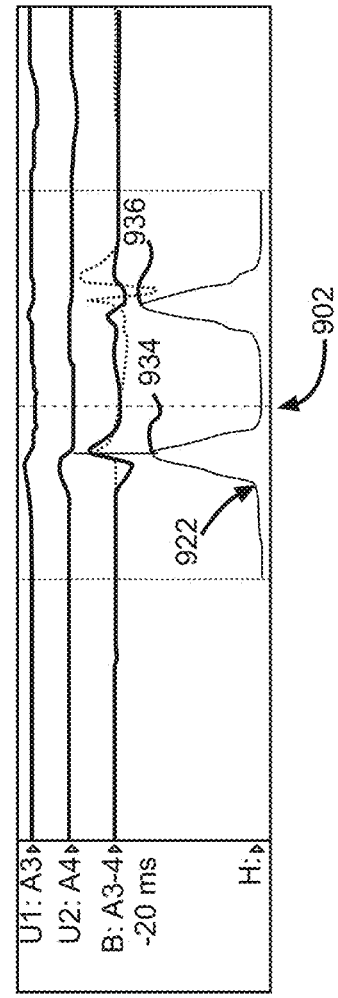
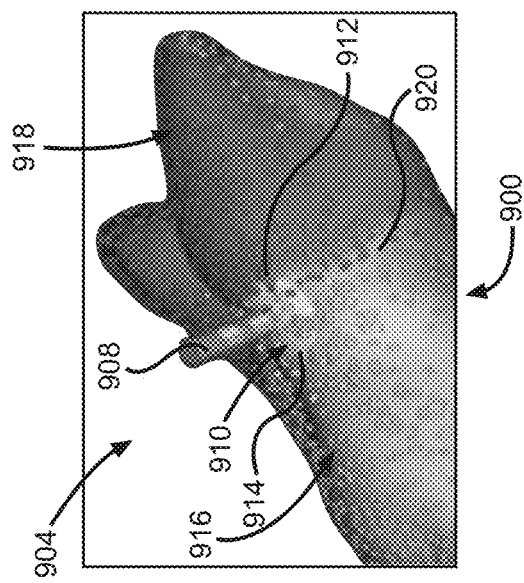
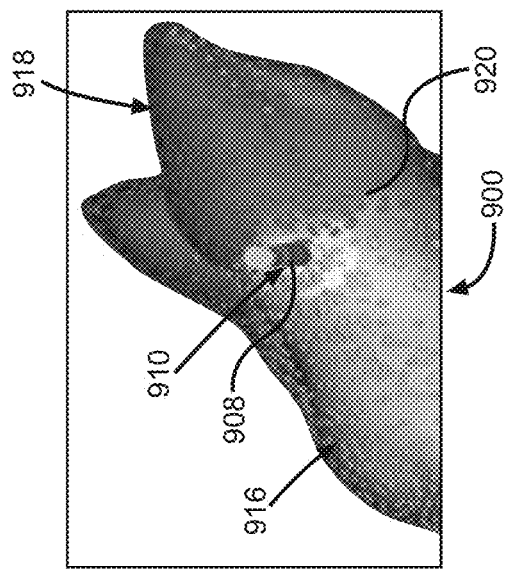
FIG. 9A
FIG. 9B

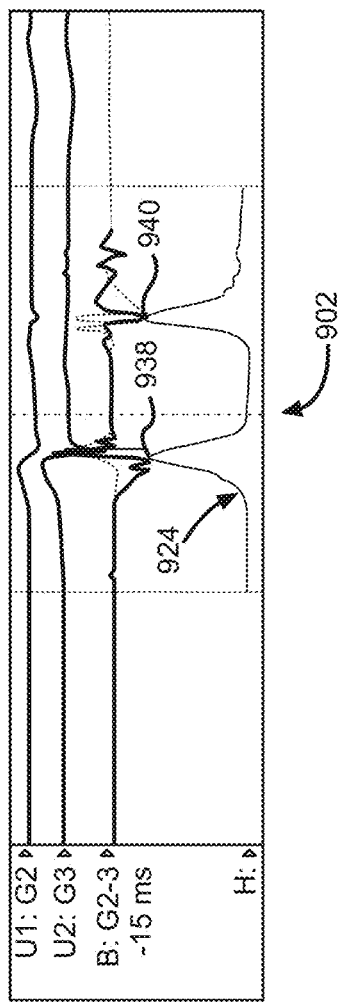
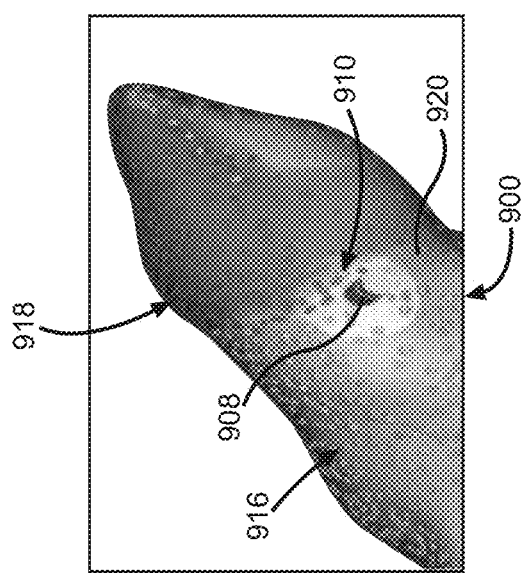
FIG. 9C

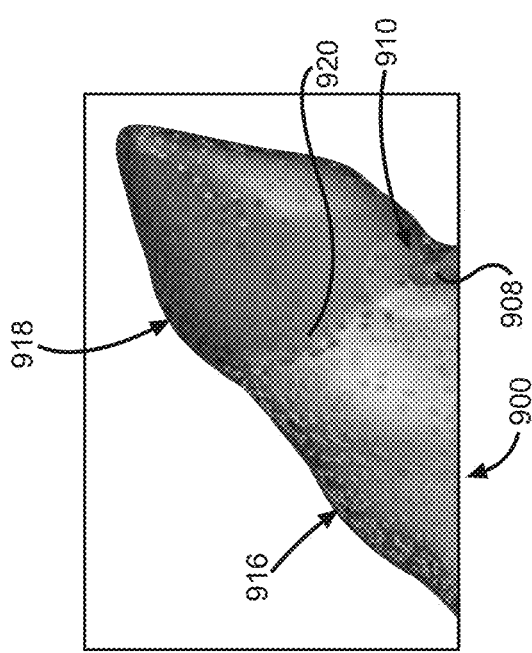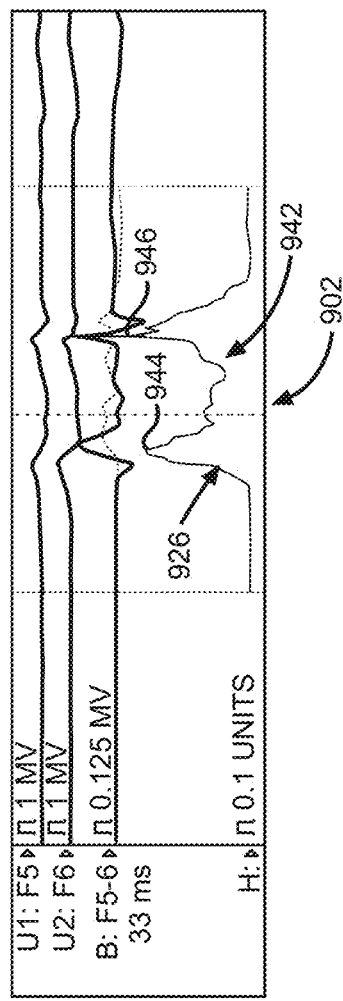
FIG. 9D
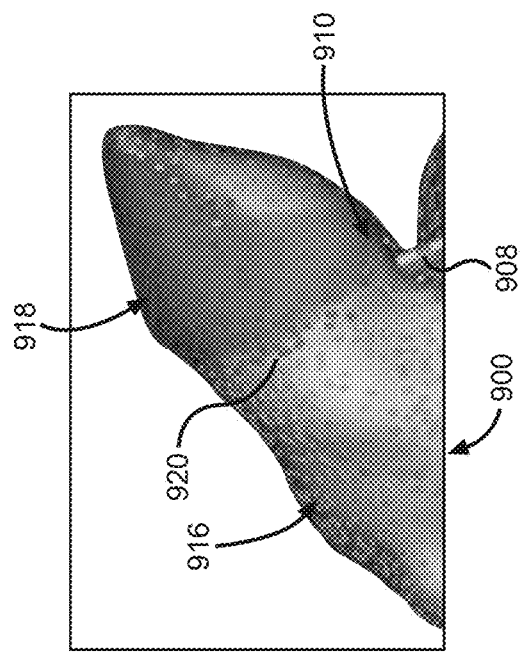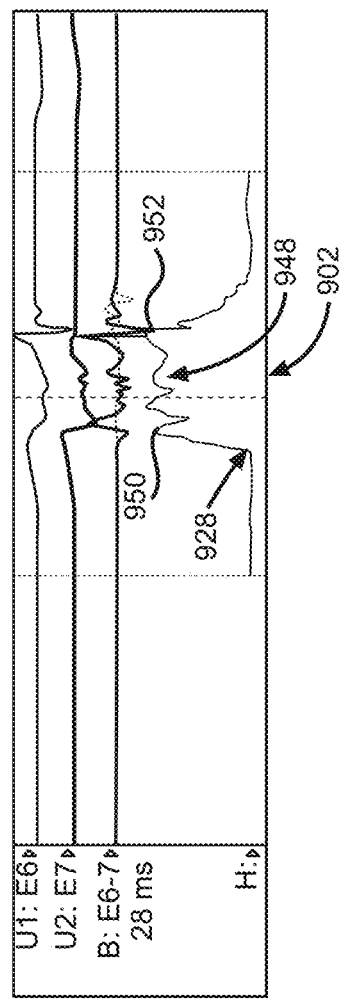
FIG. 9E

ANNOTATION HISTOGRAM

CROSS-REFERENCE TO RELATED APPLICATION

This application claims priority to Provisional Application No. 62/486,920, filed Apr. 18, 2017, which is herein incorporated by reference in its entirety.

TECHNICAL FIELD

The present disclosure relates to medical systems and methods for mapping an anatomical space of the body. More specifically, the disclosure relates to systems and methods for cardiac mapping.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional three-dimensional (3D) mapping techniques include contact mapping and non-contact mapping, and may employ a combination of contact and non-contact mapping. In both techniques, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm.

In many conventional mapping systems, the clinician visually inspects or examines the captured electrograms (EGMs), which increases examination time and cost. During an automatic electro-anatomical mapping process, however, approximately 6,000 to 20,000 intracardiac electrograms (EGMs) may be captured, which does not lend itself to being manually inspected in full by a clinician (e.g., a physician) for a diagnostic assessment, EGM categorization, and/or the like. Typically mapping systems extract scalar values from each EGM to construct voltage, activation, or other map types to depict overall patterns of activity within the heart. While maps reduce the need to inspect the captured EGMs, they also condense the often complex and useful information in the EGMs. Furthermore, maps may be misleading due to electrical artifacts or inappropriate selection of features such as activation times. Additionally, due to the complex nature of conventional techniques, cardiac maps often are not suitable for accurate and efficient interpretation.

SUMMARY

In an Example 1, a system for facilitating processing of cardiac information based on sensed electrical signals, the system comprising: a processing unit configured to: receive a set of electrical signals; receive an indication of a measurement location corresponding to each electrical signal of the set of electrical signals; and generate, based on at least one of an annotation waveform corresponding to each electrical signal of the set of electrical signals and a set of annotation mapping values, an annotation histogram.

In an Example 2, the system of Example 1, wherein the processing unit is further configured to: generate, based on the set of electrical signals and corresponding locations, an electroanatomical cardiac map of a cardiac structure; and facilitate presentation, on a display device, of a graphical user interface (GUI) that includes the cardiac map and at least one of a representation of the annotation histogram.

In an Example 3, the system of Example 2, wherein the annotation histogram represents a surface area of the cardiac map corresponding to certain annotation values.

In an Example 4, the system of Example 3, wherein the processing unit is further configured to: facilitate presentation, on the display device, of an interactive representation of a caliper; receive, via a user input device, an indication of a user selection of a portion of the representation of the annotation histogram; and facilitate, based on the annotation histogram, presentation of a representation of an amount of surface area of the map corresponding to the selected portion of the annotation histogram.

In an Example 5, the system of Example 4, wherein the representation of the amount of surface area of the map corresponding to the selected portion of the annotation histogram comprises at least one of a highlighted portion of the cardiac map and a numerical representation of the amount of surface area.

In an Example 6, the system of Example 4, wherein the representation of the amount of surface area of the map corresponding to the selected portion of the annotated histogram comprises at least one of a representation of an absolute amount of surface area and a representation of a relative amount of surface area.

In an Example 7, the system of any of Examples 2-6, the GUI including the representation of the annotation histogram, wherein the representation of the annotation histogram comprises at least one of a discrete histogram and a continuous histogram, wherein a continuous histogram is represented as a displayed waveform.

In an Example 8, the system of Example 7, wherein the processing unit determines whether to facilitate presentation of a representation of a discrete histogram or a continuous histogram based on number of values included in one or more of the bins of the annotation histogram.

In an Example 9, the system of any of Examples 2-8, the GUI further including a selection tool, and wherein the processor is configured to: determine that the selection tool is positioned in a first position; determine a selected region based on the first position and one or more selection parameters; and generate the annotation waveform, the annotation waveform corresponding to a subset of the set of electrical signals associated with the selected region.

In an Example 10, the system of Example 9, wherein the processing unit is further configured to facilitate presentation, in response to determining that the selection tool is positioned in the first position, of at least one of the representation of the annotation waveform and the representation of the annotation histogram.

In an Example 11, the system of any of the preceding Examples, wherein the annotation comprises at least one of activation, voltage, fractionation, and velocity.

In an Example 12, a system of facilitating display of cardiac information, the system comprising: a display device configured to present a representation of a cardiac map; and a processing unit configured to: receive a set of electrical signals; receive an indication of a measurement location corresponding to each electrical signal of the set of electrical signals; generate, based on the set of electrical signals, the cardiac map; facilitate presentation, on the display device, of a graphical user interface (GUI) that includes the cardiac map and a selection tool; determine that the selection tool is positioned in a first position; determine a selected region based on the first position and one or more selection parameters; and generate the annotation waveform, the annotation waveform corresponding to a subset of the set of electrical signals associated with the selected region.

In an Example 13, the system of Example 12, wherein the processing unit is further configured to facilitate presentation, in response to determining that the virtual probe is positioned in the first position, of at least one of the representation of the annotation waveform and a representation of an annotation histogram.

In an Example 14, the system of either of Examples 12 or 13, wherein the annotation comprises at least one of activation, voltage, fractionation, and velocity.

In an Example 15, a method of facilitating processing of cardiac information, the method comprising: receiving a set of electrical signals; receiving an indication of a measurement location corresponding to each of the set of electrical signals; and generating, based on at least one of an annotation waveform corresponding to each electrical signal of the set of electrical signals and a set of annotation mapping values, an annotation histogram.

In an Example 16, a system for facilitating processing of cardiac information based on sensed electrical signals, the system comprising: a processing unit configured to: receive a set of electrical signals; receive an indication of a measurement location corresponding to each electrical signal of the set of electrical signals; and generate, based on at least one of an annotation waveform corresponding to the set of the electrical signals and a set of annotation mapping values, an annotation histogram.

In an Example 17, the system of Example 16, wherein the processing unit is further configured to: generate, based on the set of electrical signals and corresponding locations, an electroanatomical cardiac map; and facilitate presentation, on a display device, of a graphical user interface (GUI) that includes the cardiac map and at least one of a representation of the annotation histogram.

In an Example 18, the system of Example 17, wherein the annotation histogram represents a surface area of the cardiac map corresponding to certain annotation values.

In an Example 19, the system of Example 18, wherein the processing unit is further configured to: facilitate presentation, on the display device, of an interactive representation of a caliper; receive, via a user input device, an indication of a user selection of a portion of the representation of the annotation histogram; and facilitate, based on the annotation histogram, presentation of a representation of an amount of surface area of the map corresponding to the selected portion of the annotation histogram.

In an Example 20, the system of Example 19, wherein the representation of the amount of surface area of the map corresponding to the selected portion of the annotation histogram comprises at least one of a highlighted portion of the cardiac map and a numerical representation of the amount of surface area.

In an Example 21, the system of Example 19, wherein the representation of the amount of surface area of the map corresponding to the selected portion of the annotated histogram comprises at least one of a representation of an absolute amount of surface area and a representation of a relative amount of surface area.

In an Example 22, the system of Example 17, the GUI including the representation of the annotation histogram, wherein the representation of the annotation histogram comprises at least one of a discrete histogram and a continuous histogram, wherein a continuous histogram is represented as a displayed waveform.

In an Example 23, the system of Example 22, wherein the processing unit determines whether to facilitate presentation of a representation of a discrete histogram or a continuous histogram based on number of values included in one or more of the bins of the annotation histogram.

In an Example 24, the system of Example 17, the GUI further including a selection tool, and wherein the processor is configured to: determine that the selection tool is positioned in a first position; determine a selected region based on the first position and one or more selection parameters; and generate the annotation waveform, the annotation waveform corresponding to a subset of the set of electrical signals associated with the selected region.

In an Example 25, the system of Example 24, wherein the processing unit is further configured to facilitate presentation, in response to determining that the selection tool is positioned in the first position, of at least one of the representation of the annotation waveform and the representation of the annotation histogram.

In an Example 26, the system of Example 16, wherein the annotation comprises at least one of activation, voltage, fractionation, and velocity.

In an Example 27, a system of facilitating display of cardiac information, the system comprising: a display device configured to present a representation of a cardiac map; and a processing unit configured to: receive a set of electrical signals; receive an indication of a measurement location corresponding to each electrical signal of the set of electrical signals; generate, based on the set of electrical signals, the cardiac map; facilitate presentation, on the display device, of a graphical user interface (GUI) that includes the cardiac map and a virtual probe; determine that the virtual probe is positioned in a first position; determine a selected region based on the first position and one or more selection parameters; and generate the annotation waveform, the annotation waveform corresponding to a subset of the set of electrical signals associated with the selected region.

In an Example 28, the system of Example 27, wherein the processing unit is further configured to facilitate presentation, in response to determining that the virtual probe is positioned in the first position, of at least one of the representation of the annotation waveform and a representation of an annotation histogram.

In an Example 29, the system of Example 28, wherein the annotation comprises at least one of activation, voltage, fractionation, and velocity.

In an Example 30, a method of facilitating processing of cardiac information, the method comprising: receiving a set of electrical signals; receiving an indication of a measurement location corresponding to each of the set of electrical signals; and generating, based on at least one of an annotation waveform corresponding to the set of electrical signals and a set of annotation mapping values, an annotation histogram.

In an Example 31, the method of Example 30, further comprising: generating, based on the set of electrical signals and corresponding locations, an electroanatomical cardiac map of a cardiac structure; and facilitating presentation, on a display device, of a graphical user interface (GUI) that includes the at least one of the cardiac map and a representation of the annotation histogram.

In an Example 32, the method of Example 31, further comprising: facilitating presentation, on the display device, of an interactive representation of a caliper; receiving, via a user input device, an indication of a user selection of a portion of the representation of the annotation histogram; and facilitating, based on the annotation histogram, presentation of a representation of an amount of surface area of the map corresponding to the selected portion of the annotation histogram.

In an Example 33, the method of Example 32, wherein the representation of the amount of surface area of the map corresponding to the selected portion of the annotation histogram comprises at least one of a highlighted portion of the cardiac map and a numerical representation of the amount of surface area, the representation of the amount of surface area of the map corresponding to the selected portion of the annotated histogram comprising at least one of a representation of an absolute amount of surface area and a representation of a relative amount of surface area.

In an Example 34, the method of Example 31, wherein the representation of the annotation histogram comprises at least one of a discrete histogram and a continuous histogram, wherein a continuous histogram is represented as a displayed waveform.

In an Example 35, the method of Example 34, further comprising determining whether to facilitate presentation of a representation of a discrete histogram or a continuous histogram based on number of values included in one or more of the bins of the annotation histogram.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIG. 5C depicts an illustrative graphical representation of the activation waveform depicted in FIG. 5B, in accordance with embodiments of the subject matter disclosed herein.

FIG. 5D depicts an illustrative graphical representation of a filtered activation waveform based on the activation waveform depicted in FIGS. 5B and 5C, in accordance with embodiments of the subject matter disclosed herein.

FIG. 7A depicts a portion of a GUI that is presenting unipolar and bipolar EGMs, in accordance with embodiments of the subject matter disclosed herein.

FIG. 7B depicts an illustrative representation of an activation histogram corresponding to a selected region around the EGMs depicted in FIG. 7A, in accordance with embodiments of the subject matter disclosed herein.

FIG. 8 depicts a portion of a cardiac map rendered by a processing unit using a display device, in accordance with embodiments of the subject matter disclosed herein.

FIGS. 9A-9E depict illustrative sequential instances of a first portion and a second portion of a GUI, including a portion of a cardiac map and a representation of an activation histogram, respectively, in accordance with embodiments of the subject matter disclosed herein.

Figure 1:
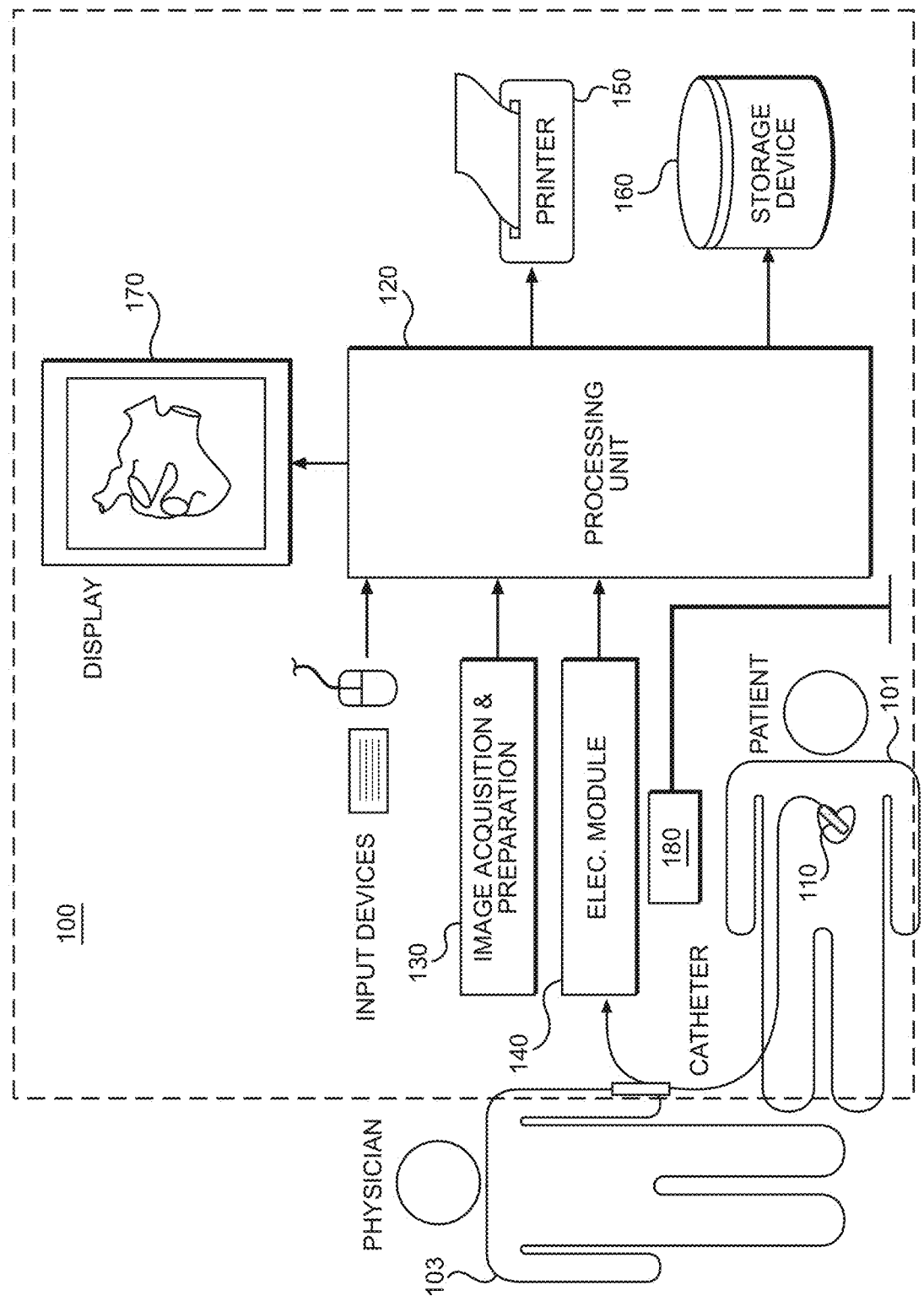
FIG. 1 is a conceptual schematic diagram depicting an illustrative cardiac mapping system, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

Embodiments of systems and methods described herein facilitate processing sensed cardiac electrical signals to return the per-sample "probability" of tissue activation by generating activation waveforms. An activation waveform is a set of activation waveform values and may include, for example, a set of discrete activation waveform values (e.g., a set of activation waveform values, a set of activation time annotations, etc.), a function defining an activation waveform curve, and/or the like. Accordingly, in embodiments, the term "activation waveform" may include a "filtered activation waveform," as described below. Similarly, as explained herein, embodiments of systems and methods described herein facilitate generating other types of annotation waveforms. An annotation waveform is a set of annotation waveform values and may include, for example, a set of discrete activation annotation values (e.g., a set of annotation waveform values, a set of time annotations, etc.), a function defining an annotation waveform curve, and/or the like. Accordingly, in embodiments, the term "annotation waveform" may include a "filtered annotation waveform." Although much of the description herein relates to activation waveforms and activation histograms, this is only for the purpose of clarity of description, and it is to be understood that any number of different aspects of embodiments described in relation to activation waveforms and/or activation histograms may apply more generally to annotation waveforms and/or annotation histograms, respectively.

Embodiments facilitate finding meaningful deflections while rejecting noises and artifacts. In embodiments, the annotation waveform may be displayed, used to present an activation waveform propagation map, used to facilitate diagnoses, used to facilitate classification of electrical signals, and/or the like. According to embodiments, to perform aspects of embodiments of the methods described herein, the cardiac electrical signals may be obtained from a mapping catheter (e.g., associated with a mapping system), a recording system, a coronary sinus (CS) catheter or other reference catheter, an ablation catheter, a memory device (e.g., a local memory, a cloud server, etc.), a communication component, a medical device (e.g., an implantable medical device, an external medical device, a telemetry device, etc.), and/or the like.

As the term is used herein, a sensed cardiac electrical signal may refer to one or more sensed signals. Each cardiac electrical signal may include a number of intracardiac electrograms (EGMs) sensed within a patient's heart, and may include any number of features that may be ascertained by aspects of the system 100. Examples of cardiac electrical signal features include, but are not limited to, activation times, activations, activation waveforms, filtered activation waveforms, minimum voltage values, maximum voltages values, maximum negative time-derivatives of voltages, instantaneous potentials, voltage amplitudes, dominant frequencies, peak-to-peak voltages, and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

Each cardiac signal also may be associated with a set of respective position coordinates that corresponds to the location at which the cardiac electrical signal was sensed. Each of the respective position coordinates for the sensed cardiac signals may include three-dimensional Cartesian coordinates, polar coordinates, and/or the like. In embodiments, other coordinate systems can be used. In embodiments, an arbitrary origin is used and the respective position coordinates refer to positions in space relative to the arbitrary origin. Since, in embodiments, the cardiac signals may be sensed on the cardiac surfaces, the respective position coordinates may be on the endocardial surface, epicardial surface, in the mid-myocardium of the patient's heart, and/or in the vicinity of one of one of these.

FIG. 1 shows a schematic diagram of an exemplary embodiment of a cardiac mapping system 100. As indicated above, embodiments of the subject matter disclosed herein may be implemented in a mapping system (e.g., the mapping system 100), while other embodiments may be implemented in an ablation system, a recording system, a computer analysis system, and/or the like. The mapping system 100 includes a moveable catheter 110 having multiple spatially distributed electrodes. During a signal-acquisition stage of a cardiac mapping procedure, the catheter 110 is displaced to multiple locations within the heart chamber into which the catheter 110 is inserted. In some embodiments the distal end of the catheter 110 is fitted with multiple electrodes spread somewhat uniformly over the catheter. For example, the electrodes may be mounted on the catheter 110 following a 3D olive shape, a basket shape, and/or the like. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, shape memory material such as Nitinol, actuable hinged structure, and/or the like. According to embodiments, the catheter 110 may be a mapping catheter, an ablation catheter, a diagnostic catheter, a CS catheter, and/or the like. For example, aspects of embodiments of the catheter 110, the electrical signals obtained using the catheter 110, and subsequent processing of the electrical signals, as described herein, may also be applicable in implementations having a recording system, ablation system, and/or any other system having a catheter with electrodes that may be configured to obtain cardiac electrical signals.

At each of the locations to which the catheter 110 is moved, the catheter's multiple electrodes acquire signals resulting from the electrical activity in the heart. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third ($\frac{1}{3}$) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements may be synchronized with one another so that the measurement are performed at approximately the same phase of the heart cycle. The signal measurements over multiple beats may be synchronized based on features detected from physiological data such as surface electrocardiograms (ECGs) and/or intracardiac electrograms (EGMs).

The cardiac mapping system 100 further includes a processing unit 120 which performs several of the operations pertaining to the mapping procedure, including the reconstruction procedure to determine the physiological information at the endocardium surface (e.g., as described above) and/or within a heart chamber. The processing unit 120 also may perform a catheter registration procedure. The processing unit 120 also may generate a 3D grid used to aggregate the information captured by the catheter 110 and to facilitate display of portions of that information.

The location of the catheter 110 inserted into the heart chamber can be determined using a conventional sensing and tracking system 180 that provides the 3D spatial coordinates of the catheter and/or its multiple electrodes with respect to the catheter's coordinate system as established by the sensing and tracking system. These 3D spatial locations may be used in building the 3D grid. Embodiments of the system 100 may use a hybrid location technology that combines impedance location with magnetic location technology. This combination may enable the system 100 to accurately track catheters that are connected to the system 100. Magnetic location technology uses magnetic fields generated by a localization generator positioned under the patient table to track catheters with magnetic sensors. Impedance location technology may be used to track catheters that may not be equipped with a magnetic location sensor, and may utilize surface ECG patches.

In embodiments, to perform a mapping procedure and reconstruct physiological information on the endocardium surface, the processing unit 120 may align the coordinate system of the catheter 110 with the endocardium surface's coordinate system. The processing unit 110 (or some other processing component of the system 100) may determine a coordinate system transformation function that transforms the 3D spatial coordinates of the catheter's locations into coordinates expressed in terms of the endocardium surface's coordinate system, and/or vice-versa. In embodiments, such a transformation may not be necessary, as embodiments of the 3D grid described herein may be used to capture contact and non-contact EGMs, and select mapping values based on statistical distributions associated with nodes of the 3D grid. The processing unit 120 also may perform post-processing operations on the physiological information to extract and display useful features of the information to the operator of the system 100 and/or other persons (e.g., a physician).

According to embodiments, the signals acquired by the multiple electrodes of catheter 110 are passed to the processing unit 120 via an electrical module 140, which may include, for example, a signal conditioning component. The electrical module 140 receives the signals communicated from the catheter 110 and performs signal enhancement operations on the signals before they are forwarded to the processing unit 120. The electrical module 140 may include signal conditioning hardware, software, and/or firmware that may be used to amplify, filter and/or sample intracardiac potential measured by one or more electrodes. The intracardiac signals typically have a maximum amplitude of 60 mV, with a mean of a few millivolts.

In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal may be filtered to remove the frequency corresponding to the power supply (e.g., 60 Hz). Other types of signal processing operations such as spectral equalization, automatic gain control, etc. may also take place. For example, in embodiments, the intracardiac signals may be unipolar signals, measured relative to a reference (which may be a virtual reference) such as, for example, a coronary sinus catheter or Wilson's Central Terminal (WCT), from which the signal processing operations may compute differences to generate multipolar signals (e.g., bipolar signals, tripolar signals, etc.). The signals may be otherwise processed (e.g., filtered, sampled, etc.) before and/or after generating the multipolar signals. The resultant processed signals are forwarded by the module 140 to the processing unit 120 for further processing.

As further shown in FIG. 1, the cardiac mapping system 100 also may include peripheral devices such as a printer 150 and/or display device 170, both of which may be interconnected to the processing unit 120. Additionally, the mapping system 100 includes storage device 160 that may be used to store data acquired by the various interconnected modules, including the volumetric images, raw data measured by electrodes and/or the resultant endocardium representation computed therefrom, the partially computed transformations used to expedite the mapping procedures, the reconstructed physiological information corresponding to the endocardium surface, and/or the like.

In embodiments, the processing unit 120 may be configured to automatically improve the accuracy of its algorithms by using one or more artificial intelligence (i.e., machine-learning) techniques, classifiers, and/or the like. In embodiments, for example, the processing unit may use one or more supervised and/or unsupervised techniques such as, for example, support vector machines (SVMs), k-nearest neighbor techniques, artificial neural networks, and/or the like. In embodiments, classifiers may be trained and/or adapted using feedback information from a user, other metrics, and/or the like.

The illustrative cardiac mapping system 100 shown in FIG. 1 is not intended to suggest any limitation as to the scope of use or functionality of embodiments of the present disclosure. Neither should the illustrative cardiac mapping system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein. For example, the electrical module 140 may be integrated with the processing unit 120. Additionally, or alternatively, aspects of embodiments of the cardiac mapping system 100 may be implemented in a computer analysis system configured to receive cardiac electrical signals and/or other information from a memory device (e.g., a cloud server, a mapping system memory, etc.), and perform aspects of embodiments of the methods described herein for processing cardiac information (e.g., determining annotation waveforms, etc.). That is, for example, a computer analysis system may include a processing unit 120, but not a mapping catheter.

Figure 2:
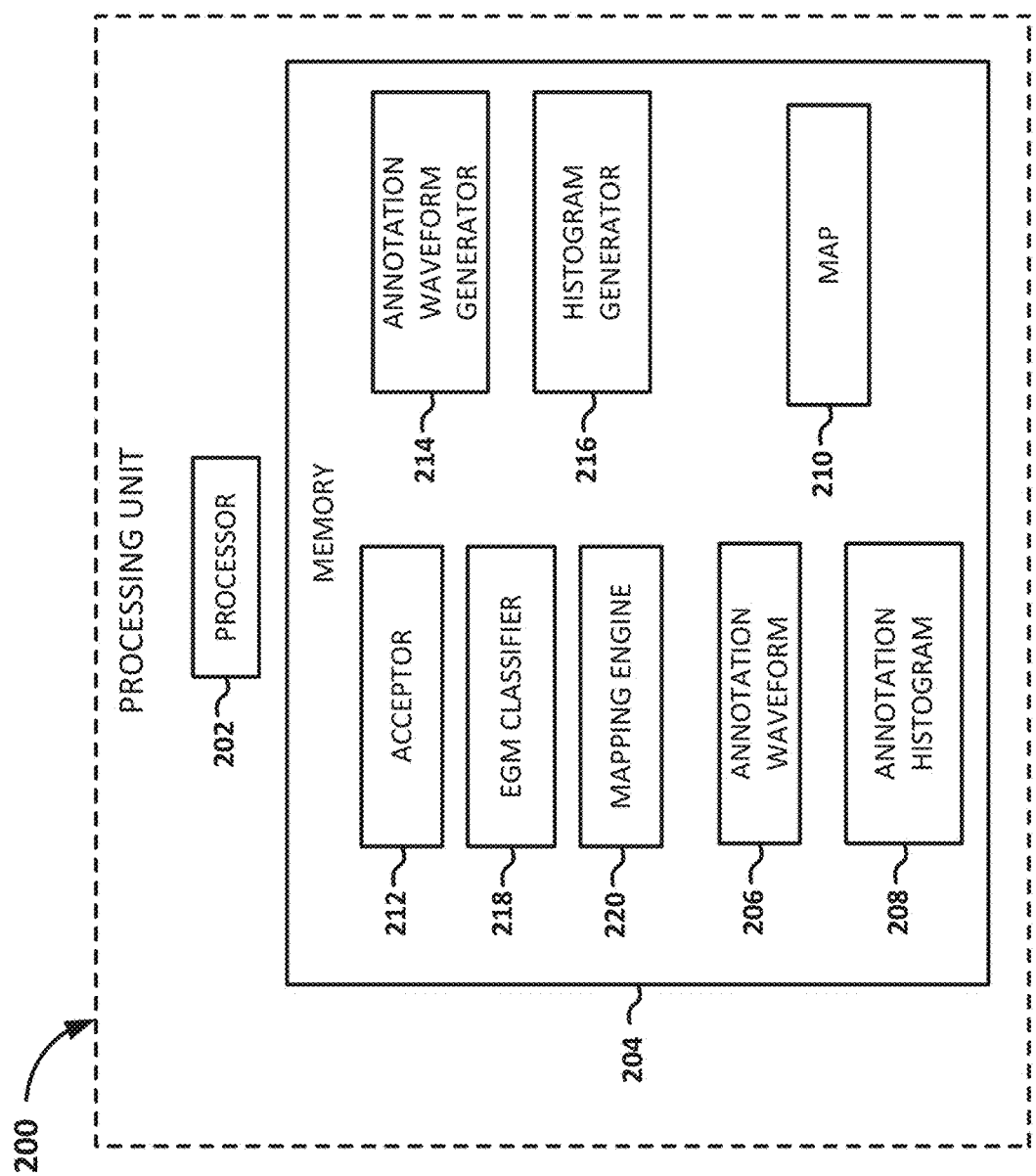
FIG. 2 is a block diagram depicting an illustrative processing unit for use with a cardiac mapping system, in accordance with embodiments of the subject matter disclosed herein.

FIG. 2 is a block diagram of an illustrative processing unit 200, in accordance with embodiments of the disclosure. The processing unit 200 may be, be similar to, include, or be included in the processing unit 120 depicted in FIG. 1. As shown in FIG. 2, the processing unit 200 may be implemented on a computing device that includes a processor 202 and a memory 204. Although the processing unit 200 is referred to herein in the singular, the processing unit 200 may be implemented in multiple instances (e.g., as a server cluster), distributed across multiple computing devices, instantiated within multiple virtual machines, and/or the like. One or more components for facilitating cardiac mapping may be stored in the memory 204. In embodiments, the processor 202 may be configured to instantiate the one or more components to generate an annotation waveform 206, an annotation histogram 208, and a cardiac map 210, any one or more of which may be stored in the memory 204.

As is further depicted in FIG. 2, the processing unit 200 may include an acceptor 212 configured to receive electrical signals from a mapping catheter (e.g., the mapping catheter 110 depicted in FIG. 1). The measured electrical signals may include a number of intracardiac electrograms (EGMs) sensed within a patient's heart. The acceptor 212 may also receive an indication of a measurement location corresponding to each of the electrical signals. In embodiments, the acceptor 212 may be configured to determine whether to accept the electrical signals that have been received. The acceptor 212 may utilize any number of different components and/or techniques to determine which electrical signals or beats to accept, such as filtering, beat matching, morphology analysis, positional information (e.g., catheter motion), respiration gating, and/or the like.

The accepted electrical signals are received by an annotation waveform generator 214 that is configured to extract at least one annotation feature from each of the electrical signals, in cases in which the electrical signal includes an annotation feature to extract. In embodiments, the at least one annotation feature includes at least one value corresponding to at least one annotation metric. The at least one feature may include at least one event, where the at least one event includes the at least one value corresponding to the at least one metric and/or at least one corresponding time (a corresponding time does not necessarily exist for each annotation feature). According to embodiments, the at least one metric may include, for example, an activation time, minimum voltage value, maximum voltage value, maximum negative time-derivative of voltage, an instantaneous potential, a voltage amplitude, a dominant frequency, a peak-to-peak voltage, an activation duration, and/or the like. According to embodiments, the annotation waveform generator 214 may be configured to detect activations and to generate an annotation waveform 206, which may be, for example, an activation waveform.

As shown in FIG. 2, the processing unit 200 includes a histogram generator 216 that is configured to generate an annotation histogram 208 having a number of bins within which annotations from electrograms (EGMs) are included. The processing unit 200, using the histogram generator 216, may be configured to aggregate a set of annotation features by including each of the features and/or EGMs in a histogram. For example, the histogram generator 216 may be configured to aggregate the set of activation features by assigning a confidence level to each event corresponding to an activation feature; determining a weighted confidence level associated with each event; and including the weighted confidence levels in a histogram. The processing unit includes an electrogram (EGM) classifier 218 that is configured to classify EGMs according to any number of different classifications based, for example, on characteristic of the EGM, the annotation waveform 206, annotation histogram 208, and/or the like. Additionally, the processing unit 200 includes a mapping engine 220 that is configured to facilitate presentation of a map 210 corresponding to a cardiac surface based on the electrical signals. In embodiments, the map 210 may include a voltage map, an activation map, a fractionation map, velocity map, confidence map, and/or the like.

The illustrative processing unit 200 shown in FIG. 2 is not intended to suggest any limitation as to the scope of use or functionality of embodiments of the present disclosure. Neither should the illustrative processing unit 200 be interpreted as having any dependency or requirement related to any single component or combination of components illustrated therein. Additionally, any one or more of the components depicted in FIG. 2 may be, in embodiments, integrated with various ones of the other components depicted therein (and/or components not illustrated), all of which are considered to be within the ambit of the subject matter disclosed herein. For example, the acceptor 212 may be integrated with the EGM classifier 218 and/or the mapping engine 220. In embodiments, the processing unit 200 may not include an acceptor 212, while in other embodiments, the acceptor 212 may be configured to receive electrical signals from a memory device, a communication component, and/or the like.

Additionally, the processing unit 200 may (alone and/or in combination with other components of the system 100 depicted in FIG. 1, and/or other components not illustrated) perform any number of different functions and/or processes associated with cardiac mapping (e.g., triggering, blanking, field mapping, etc.) such as, for example, those described in U.S. Pat. No. 8,428,700, entitled "ELECTROANATOMICAL MAPPING;" U.S. Pat. No. 8,948,837, entitled "ELECTROANATOMICAL MAPPING;" U.S. Pat. No. 8,615,287, entitled "CATHETER TRACKING AND ENDOCARDIUM REPRESENTATION GENERATION;" U.S. Patent Publication 2015/0065836, entitled "ESTIMATING THE PREVALENCE OF ACTIVATION PATTERNS IN DATA SEGMENTS DURING ELECTROPHYSIOLOGY MAPPING;" U.S. Pat. No. 6,070,094, entitled "SYSTEMS AND METHODS FOR GUIDING MOVABLE ELECTRODE ELEMENTS WITHIN MULTIPLE-ELECTRODE STRUCTURE;" U.S. Pat. No. 6,233,491, entitled "CARDIAC MAPPING AND ABLATION SYSTEMS;" U.S. Pat. No. 6,735,465, entitled "SYSTEMS AND PROCESSES FOR REFINING A REGISTERED MAP OF A BODY CAVITY;" the disclosures of which are hereby expressly incorporated herein by reference.

According to embodiments, various components of the mapping system 100, illustrated in FIG. 1, and/or the processing unit 200, illustrated in FIG. 2, may be implemented on one or more computing devices. A computing device may include any type of computing device suitable for implementing embodiments of the disclosure. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2 with reference to various components of the system 100 and/or processing unit 200.

In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices.

In embodiments, memory (e.g., the storage device 160 depicted in FIG. 1, and/or the memory 204 depicted in FIG. 2) includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 160 and/or 204 stores computer-executable instructions for causing a processor (e.g., the processing unit 120 depicted in FIG. 1 and/or the processor 202 depicted in FIG. 2) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Examples of such program components include the annotation waveform 206, the annotation histogram 208, the map 210, the acceptor 212, the annotation waveform generator 214, the histogram generator 216, the EGM classifier 218, and the mapping engine 220. Program components may be programmed using any number of different programming environments, including various languages, development kits, frameworks, and/or the like. Some or all of the functionality contemplated herein may also, or alternatively, be implemented in hardware and/or firmware.

Figure 3:
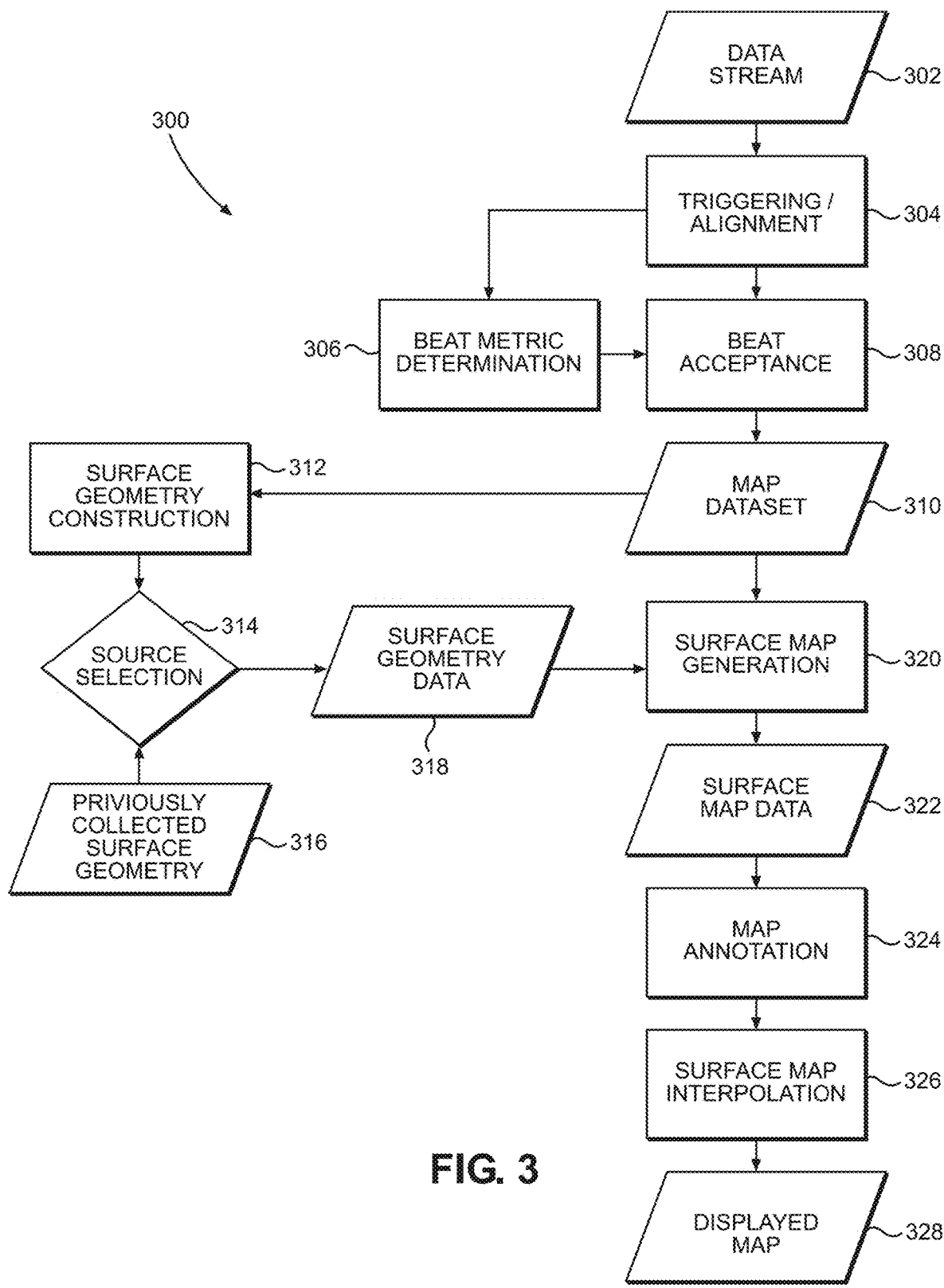
FIG. 3 is a flow diagram depicting an illustrative process for generating a cardiac map, in accordance with embodiments of the subject matter disclosed herein.

FIG. 3 is a flow diagram of an illustrative process 300 for automated electro-anatomical mapping, in accordance with embodiments of the disclosure. Aspects of embodiments of the method 300 may be performed, for example, by a processing unit (e.g., the processing unit 120 depicted in FIG. 1, and/or the processing unit 200 depicted in FIG. 2). A data stream 302 containing multiple signals is first input into the system (e.g., the cardiac mapping system 100 depicted in FIG. 1). During the automated electro-anatomical mapping process, a data stream 302 provides a collection of physiological and non-physiological signals that serve as inputs to the mapping process. The signals may be collected directly by the mapping system, and/or obtained from another system using an analog or digital interface. The data stream 302 may include signals such as unipolar and/or bipolar intracardiac electrograms (EGMs), surface electrocardiograms (ECGs), electrode location information originating from one or more of a variety of methodologies (magnetic, impedance, ultrasound, real time MRI, etc.), tissue proximity information, catheter force and/or contact information obtained from one or more of a variety of methodologies (force spring sensing, piezo-electric sensing, optical sensing etc.), catheter tip and/or tissue temperature, acoustic information, catheter electrical coupling information, catheter deployment shape information, electrode properties, respiration phase, blood pressure, other physiological information, and/or the like.

For the generation of specific types of maps, one or more signals may be used as one or more references, during a triggering/alignment process 304, to trigger and align the data stream 302 relative to the cardiac, other biological cycle and/or an asynchronous system clock resulting in beat datasets. Additionally, for each incoming beat dataset, a number of beat metrics are computed during a beat metric determination process 306. Beat metrics may be computed using information from a single signal, spanning multiple signals within the same beat and/or from signals spanning multiple beats. The beat metrics provide multiple types of information on the quality of the specific beat dataset and/or likelihood that the beat data is good for inclusion in the map dataset. A beat acceptance process 308 aggregates the criteria and determines which beat datasets will make up the map dataset 310. The map dataset 310 may be stored in association with a 3D grid that is dynamically generated during data acquisition.

Surface geometry data may be generated concurrently during the same data acquisition process using identical and/or different triggering and/or beat acceptance metrics employing a surface geometry construction process 312.

This process constructs surface geometry using data such as electrode locations and catheter shape contained in the data stream. Additionally, or alternatively, previously collected surface geometry 316 may be used as an input to surface geometry data 318. Such geometry may have been collected previously in the same procedure using a different map dataset, and/or using a different modality such as CT, MRI, ultrasound, rotational angiography, and/or the like, and registered to the catheter locating system. The system performs a source selection process 314, in which it selects the source of the surface geometry data and provides surface geometry data 318 to a surface map generation process 320. The surface map generation process 320 is employed to generate surface map data 322 from the map dataset 310 and surface geometry data 318.

The surface geometry construction algorithm generates the anatomical surface on which the electroanatomical map is displayed. Surface geometry can be constructed, for example, using aspects of a system as described U.S. patent application Ser. No. 12/437,794, entitled "Impedance Based Anatomy Generation" and filed on May 8, 2008; and/or U.S. Pat. No. 8,948,837, entitled "Electroanatomical Mapping" and issued on Feb. 3, 2015, the contents of each of which is incorporated by reference herein in its entirety. Additionally, or alternatively, an anatomical shell can be constructed by the processing unit by fitting a surface on electrode locations that are determined either by the user or automatically to be on the surface of the chamber. In addition, a surface can be fit on the outermost electrode and/or catheter locations within the chamber.

As described, the map dataset 310 from which the surface is constructed can employ identical or different beat acceptance criteria from those used for electrical and other types of maps. The map dataset 310 for surface geometry construction can be collected concurrently with electrical data or separately. Surface geometry can be represented as a mesh containing a collection of vertices (points) and the connectivity between them (e.g. triangles). Alternatively, surface geometry can be represented by different functions such as higher order meshes, non-uniform rational basis splines (NURBS), and/or curvilinear shapes.

The generation process 320 generates surface map data 322. The surface map data 322 may provide information on cardiac electrical excitation, cardiac motion, tissue proximity information, tissue impedance information, force information, and/or any other collected information desirable to the clinician. The combination of map dataset 310 and surface geometry data 318 allows for surface map generation. The surface map is a collection of values or waveforms (e.g., EGMs) on the surface of the chamber of interest, whereas the map dataset can contain data that is not on the cardiac surface. One approach for processing the map dataset 310 and surface geometry data 318 to obtain a surface map dataset 322 is described in U.S. Pat. No. 7,515,954, entitled "NON-CONTACT CARDIAC MAPPING, INCLUDING MOVING CATHETER AND MULTI-BEAT INTEGRATION" and filed Jun. 13, 2006, the contents of which is incorporated by reference herein in its entirety.

Alternatively, or in combination with the method above, an algorithm that applies acceptance criteria to individual electrodes can be employed. For example, electrode locations exceeding a set distance (e.g., 3 mm) from surface geometry can be rejected. Another algorithm can incorporate tissue proximity information using impedance for inclusion in the surface map data. In this case only electrode location whose proximity value is less than 3 mm might be included. Additional metrics of the underlying data can also be used for this purpose. For example, EGM properties similar to beat metrics can be assessed on a per electrode basis. In this case metrics such as far field overlap and/or EGM consistency can be used. It should be understood that variations on the method to project points from the map dataset 310 to the surface and/or to select appropriate points can exist.

Once obtained, the surface map data 322 may be further processed to annotate desired features from the underlying data, a process defined as surface map annotation 324. Once data is collected into surface map data 322, attributes relating to the collected data may be automatically presented to the user. These attributes can be automatically determined and applied to the data by the computer system and are referred to herein as annotations. Exemplary annotations include activation time, the presence of double activation or fractionation, voltage amplitude, spectral content, and/or the like. Due to the abundance of data available in automated mapping (e.g., mapping completed by the computer system with minimal human input related to the incoming data), it is not practical for the operator to review and annotate data manually. However, human input can be a valuable addition to the data, and so when user input is provided it is necessary for the computer system to automatically propagate and apply it to more than one data point at a time.

It may be possible to use the computer system to automatically annotate activation time, voltage, and other characteristics of individual EGMs. Activation time detection may use methods similar to those previously described to detect a trigger and can similarly benefit from the use of blanking and powered triggering operator. Desired annotations may include instantaneous potential, activation time, voltage amplitude, dominant frequency and/or other properties of the signal. Once computed, the annotations may be displayed superimposed on chamber geometry. In embodiments, a gap-filling surface map interpolation may be employed 326. For example, in embodiments, a gap-filling interpolation may be employed where a distance between a point on the surface to a measured EGM exceeds a threshold, as this may indicate, for example, that grid-based interpolation, as described herein, may not be as effective in that situation. Displayed maps 328 can be computed and displayed separately, and/or overlaid on top of each other.

The illustrative process 300 shown in FIG. 3 is not intended to suggest any limitation as to the scope of use or functionality of embodiments of the present disclosure. Neither should the illustrative process 300 be interpreted as having any dependency or requirement related to any single component or combination of components illustrated therein. Additionally, any one or more of the components depicted in FIG. 3 may be, in embodiments, integrated with various ones of the other components depicted therein (and/or components not illustrated), all of which are considered to be within the ambit of the present disclosure.

Figure 4:
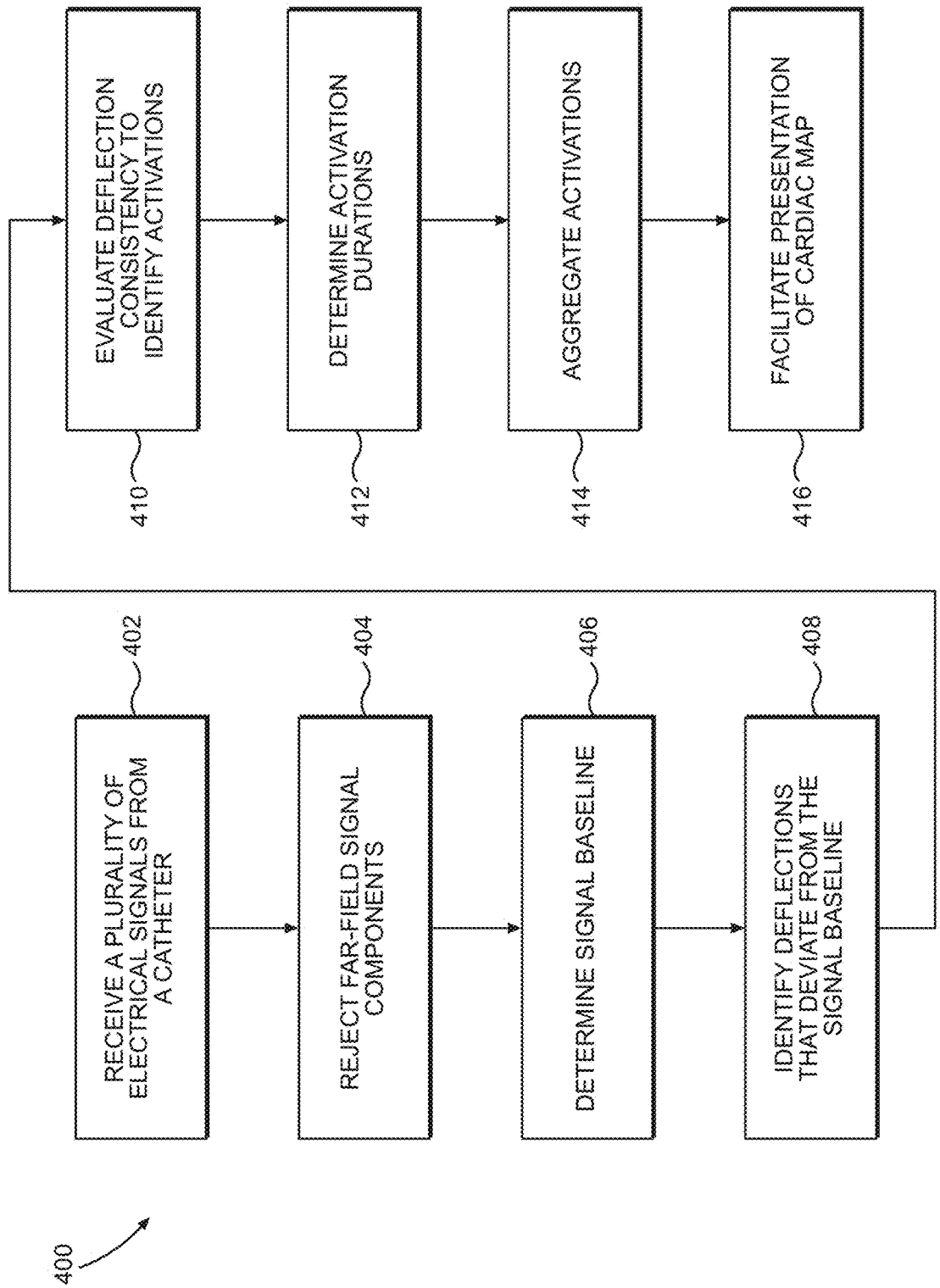
FIG. 4 is a flow diagram depicting an illustrative method of processing electrophysiological information, in accordance with embodiments of the subject matter disclosed herein.

FIG. 4 is a flow diagram depicting an illustrative method 400 of processing electrophysiological information, in accordance with embodiments of the disclosure. Aspects of embodiments of the method 400 may be performed, for example, by a processing unit (e.g., the processing unit 120 depicted in FIG. 1, and/or the processing unit 200 depicted in FIG. 2). Embodiments of the method 400 include receiving a plurality of electrical signals from a catheter (block 402). The catheter may be any catheter having one or more electrodes configured to obtain electrical signals (e.g., the mapping catheter 110 depicted in FIG. 1, a CS catheter, an ablation catheter, etc.). The processing unit also may receive an indication of a measurement location corresponding to each of the electrical signals. As explained above, with respect to FIG. 3, the processing unit and/or other components (e.g., the electrical module 140 depicted in FIG. 1) may be configured to determine whether to accept particular electrical signals (e.g., beats) based on one or more beat acceptance criteria.

According to embodiments, cardiac electric signal features may be extracted from the cardiac electrical signals (e.g., EGMs). Examples of features of the cardiac electrical signals include, but are not limited to, activation times, minimum voltage values, maximum voltages values, maximum negative time-derivatives of voltages, instantaneous potentials, voltage amplitudes, dominant frequencies, peak-to-peak voltages, and/or the like. Each of the respective points at which a cardiac electrical signal is sensed may have a corresponding set of three-dimensional position coordinates. For example, the position coordinates of the points may be represented in Cartesian coordinates. Other coordinate systems can be used, as well. In embodiments, an arbitrary origin is used and the respective position coordinates are defined with respect to the arbitrary origin. In some embodiments, the points have non-uniform spacing, while in other embodiments, the points have uniform spacing. In embodiments, the point corresponding to each sensed cardiac electrical signal may be located on the endocardial surface of the heart and/or below the endocardial surface of the heart.

Figure 5A:
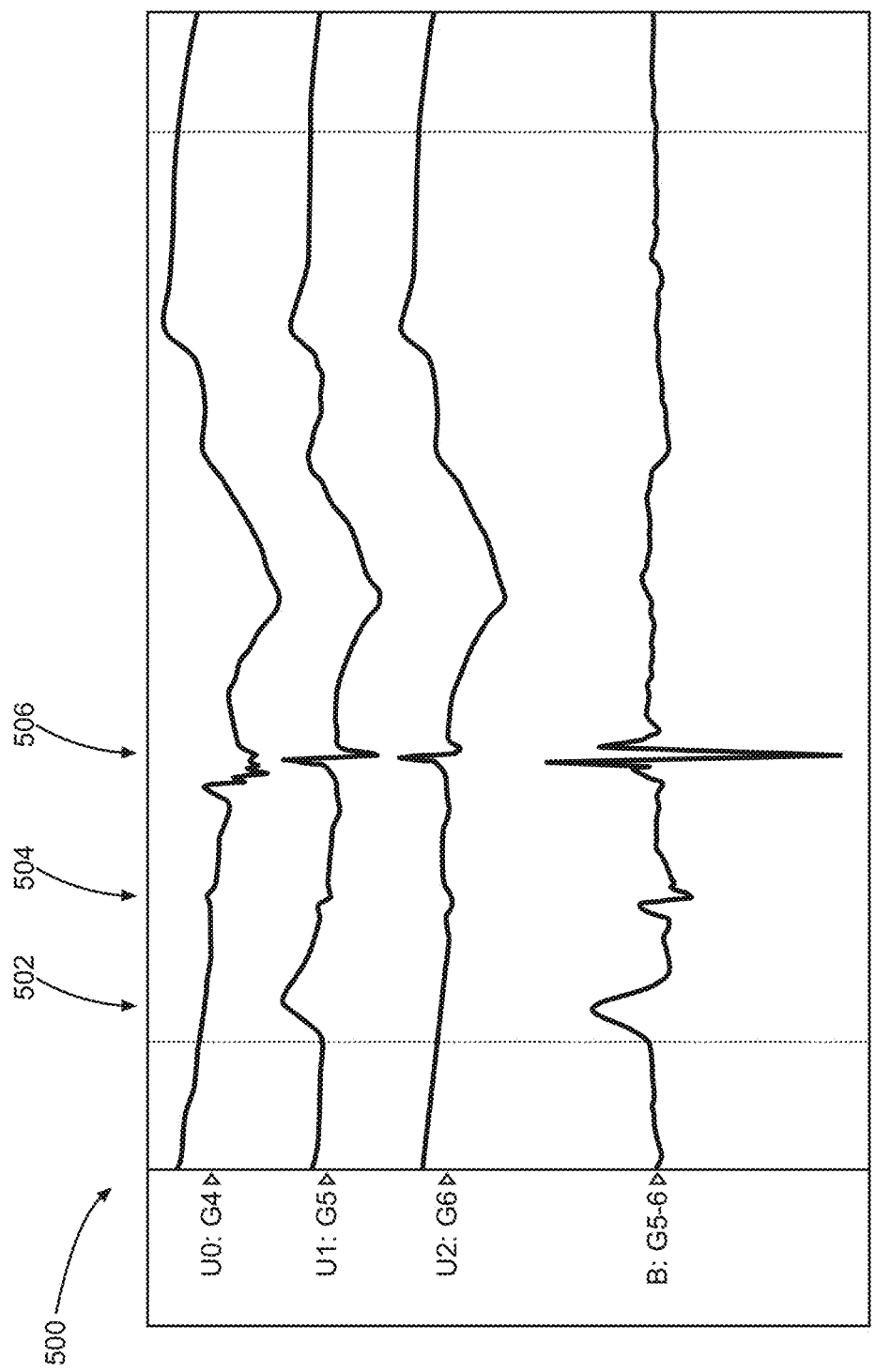
FIG. 5A depicts an illustrative graphical representation of electrical signals received from a mapping catheter, in accordance with embodiments of the subject matter disclosed herein.

FIG. 5A shows an exemplary graphical representation 500 illustrating electrical signals (in this case, EGMs) received from a mapping catheter, each representing a magnitude of a depolarization sequence of a heart during a predetermined time period. In this example, a first signal U0 may be associated with a first electrode G4, a second signal U1 may be associated with a second electrode G5, and a third signal U2 may be associated with a third electrode G6. The signals U0, U1, U2 may represent unipolar signals received from a first mapping catheter and a fourth signal B may represent a bipolar signal associated with the second and third electrodes G5 and G6. In embodiments, the bipolar signal B may represent a graphical summation of signals received from the second and third electrodes G5 and G6. In embodiments, and, for example, depending on a lead tip configuration of a catheter, the acquired electrical signals may be unipolar signals, bipolar signals, and/or other multipolar signals.

With continuing reference to FIG. 4, to filter out unwanted signals, embodiments of the method 400 also include rejecting or attenuating far-field signal components from the acquired electrical signals (block 404). For example, R-waves sensed by an atrial channel of the heart that are unrelated to the diagnostic assessment may be rejected or attenuated as unwanted signals. Other exemplary unwanted signals may include common mode noise such as power-line noise, T-waves, skeletal muscle myopotentials (e.g., from a pectoral muscle), and crosstalk signals from another device (e.g., a pacemaker) to suit different applications. In embodiments, far-field signal components may be rejected or attenuated by creating a multipolar signal (e.g., the bipolar signal B associated with the second and third electrodes G5 and G6, depicted in FIG. 5A, a tripolar signal, etc.). Any number of other techniques may be implemented for processing the electrical signals such as, for example, signal conditioning, filtering, transforming, and/or the like. In embodiments, the method 400 may include any number of other types of artifact rejection. For example, in embodiments, artifact rejection may be achieved using spatio-temporal analysis (e.g., as described below with reference to block 410), morphological analysis, continuous-mode artifact rejection, (e.g., unipolar rejection), combinations of unipolar and/or multipolar signals (e.g., nonlinear combination of all received signals), and/or the like. Any number of other types of filtering may be performed on the electrical signals. As such, for example, the term electrical signal may also include filtered electrical signals (e.g., as used in connection with subsequent processing steps).

Embodiments of the method 400 include identifying far-field signal components, but not necessarily rejecting or attenuating the identified far-field signal components. In embodiments, for example, far-field signal components may include information that can be used for various aspects of analyses of cardiac electrical signals. For example, far-field signal components may include information about neighboring anatomical structures. Far-field signal components may be identified, isolated, analyzed, and/or the like. In embodiments, the method 400 may include identifying far-field signal components, and taking some action in response thereto. That is, for example, in embodiments, far-field signal components may be used in conjunction with detection of local, spatially-varying activation for identifying tachycardia-sustaining isthmus, and/or the like.

Embodiments of the method 400 further include determining a signal baseline (block 406) during a quiescent time period. The signal baseline, which may be determined based on historical information, population information, patient information, environmental information, and/or the like, may include a value or range of values determined such that deflections of the EGM deviating beyond the baseline by a specified amount are deemed to be activations. The signal baseline may be generic, patient-specific, EGM-specific, time-varying, and/or the like. In embodiments, the signal baseline may be a pre-determined minimum value and/or maximum value.

In embodiments, a signal baseline may be determined such that deflections deviating beyond the signal baseline have some computed probability (or minimum probability) of being activations. According to embodiments, the signal baseline may include a range of values that represent, and/or are determined based on a noise floor. That is, for example, a noise floor may be estimated and the signal baseline established as the upper and lower boundaries of the noise floor, a multiple of the noise floor, and/or some other function of the noise floor (e.g., within a certain standard deviation of the noise floor, etc.). According to embodiments, for example, a signal baseline determination process may include identifying "quiet periods" within a specified window (e.g., a 0.5 second time window, a 1 second time window, etc.), and determining the signal baseline based on the quiet periods. That is, for example, within a specified window, one or more time periods may be identified in which the amplitude of the electrical signal is within a specified range, and/or within a specified distance from other amplitudes. An electrical signal may be an electrogram (EGM), a filtered EGM, a set of absolute values of an EGM, values of peaks of an EGM at peak locations, a combination of these, and/or the like. For example, an electrical signal may be represented as a set of ordered values (e.g., the amplitude of each sample point may be a value in the set), and a specified percentile and/or multiplier thereof, may be used to define the signal baseline. That is, for example, a multiplier of the $20^{th}$ percentile (e.g., the $20^{th}$ lowest value or bin of values) may be used to define the signal baseline. In embodiments, to determine the signal baseline, one or more electrical signals may be dilated, and the dilated electrical signal (e.g., dilated EGM) may be used to compute the $20^{th}$ percentile. Dilation is an operation that replaces every sample with the maximum of the samples in a specified time window (e.g., 15 ms, 20 ms, 25 ms, etc.). Dilation can also be described, for example, as a moving maximum (similar to a moving average, but in which values are replaced with the maximum value in the window instead of the average value). Similar analyses may be implemented with regard to any one or more other characteristics of an electrical signal (e.g., frequency, signal-to-noise ratio (SNR), etc.), and/or the like.

In embodiments, the signal baseline may be determined based on particular attributes of a specific patient, environmental information, corresponding portions of a cardiac cycle, aspects of a reference signal, and/or the like. Additionally, or alternatively, the signal baseline may be determined based on a certain sample of information such as, for example, information associated with a set of acquired EGMs within a specified region. The specified region also may be used to identify the EGMs used in any number of other aspects of embodiments of the method 400. The specified region may be defined (e.g., in one dimension (1D), two dimensions (2D), three dimensions (3D), etc.) according to a specified radius. In embodiments, the specified radius may be, be similar to, include, be included within, and/or be determined based on, a stochastic radius such as is described in U.S. application Ser. No. 15/230,233, entitled "CARDIAC MAPPING USING A 3D GRID," filed on Aug. 5, 2016, and which claims the priority benefit of U.S. Provisional Application No. 62/202,711, having the same title, and filed on Aug. 7, 2015, the entirety of each of which is hereby expressly incorporated herein by reference for all purposes.

In embodiments, the specified region may be defined in the context of time such as, for example, by defining the specified region to be the spatial region that includes any EGMs recorded during a specified time period (e.g., during the window of analysis). Any number of different combinations of the above characteristics of the specified region may be implemented and may include any number of other considerations (e.g., a specified arrhythmia, a specified treatment, a specified medical device, etc.).

In embodiments, the specified region may be predetermined and/or fixed. In embodiments, the specified region may be determined by calculating a maximum distance between two adjacent points on a grid or graph used for aggregating acquired electrical signals, and/or may be configured to optimize the relevance of aggregate values from the grid and/or graph that may be interpolated onto an anatomical mesh, aggregate activation information associated with activation waveforms, and/or the like. The specified region may be defined using any number of different measurements of distance (e.g., a rectilinear distance, L1, a Euclidean distance, L2, etc.), time, relevance (e.g., confidence levels, weightings, etc.).

The specified region may be adaptive and may be dynamically adjusted based on any number of different factors such as, for example, user input, mapping quality metrics (e.g., a surface projection distance (SPD), which is the maximum distance that an electrode can fall from a mesh surface and still be projected into the map, which may be set and/or adjusted to facilitate control over the accuracy of the map), environmental parameters, physiological parameters, and/or the like.

As is further shown in FIG. 4, embodiments of the method 400 include identifying one or more deflections in an electrical signal that deviate beyond the signal baseline according to one or more specified criteria (block 408). For example, a deflection may be identified wherein the amplitude of the signal exceeds a signal baseline value, wherein the amplitude of the signal deviates beyond baseline by a specified amount (e.g., a relative deviation), and/or the like. In this manner, while the identification of deflections deviating beyond the signal baseline according to one or more specified criteria may have a weak amplitude dependency, this identification is generally not dependent upon, or affected by, variations in amplitude within ranges based on the baseline signal.

In embodiments, identifying deflections that deviate beyond the signal baseline may include determining, for each sample point of an electrical signal, a corresponding activation waveform value. For example, in embodiments, the method 400 may include determining a probability (e.g., a value between 0 and 1, inclusive) that a given sample point represents an activation, based on its relation to the signal baseline. In embodiments, other numerical scales may be used for assigning the probability such as, for example, values between 0 and 100, and/or the like. In embodiments, a likelihood (e.g., a probability) that a signal deflection represents an activation may be determined based on the deviation of that deflection from the signal baseline. For example, a deflection having a maximum amplitude that deviates from the signal baseline by at least a specified amount may be assigned a probability of 1, while a deflection having a maximum amplitude that deviates from the signal baseline by at most a specified amount may be assigned a probability of 0. Probabilities may be assigned, in linear and/or nonlinear, fashions to deflections having amplitudes that are not satisfied by either of the preceding criteria based on, for example, the relative deviation of the deflection amplitude with respect to the above criteria. In this manner, for example, an activation waveform value may be a probability that an identified deflection corresponding to a sample point represents an activation.

According to embodiments, original EGM information during detected periods of deviation from baseline may be used to further refine the likelihood of activation. This information may include, for example, the slope of the EGM, the monotonicity of the EGM (e.g., whether the slope stays positive for 1 ms or for 40 ms before becoming negative), the presence of adjacent deflections, and/or the like. In embodiments, for example, detected baseline deviations having a slope close to 0 (e.g., within a specified range around 0) may have their likelihood score diminished. Detected baseline deviations that contain a monotonic EGM signal (e.g., the slope does not change sign) for specified time durations (e.g., for greater than 11 ms) may have their likelihood score diminished. In embodiments, detected deviations from baseline that are adjacent or overlapping other deviations from baseline with larger amplitude may have their likelihood score diminished. This may be done by comparing the prominence of the peak of a deflection to the prominence of the adjacent peaks and diminishing the likelihood score as this ratio falls. A deflection that fits this description can be visually described as a shoulder of a larger amplitude deflection.

In embodiments, for example, activation waveform values may represent confidence levels associated with each sample point. That is, for example, an activation waveform value of 1, or approximately 1, may indicate a relatively high (e.g., relative to confidence levels associated with other values between 0 and 1) level of confidence that the corresponding sample point represents a deflection from the signal baseline due to an activation, while an activation waveform value of 0, or approximately 0, may indicate a relatively low (e.g., relative to confidence levels associated with other values between 0 and 1) level of confidence that the corresponding sample point represents a deflection from the signal baseline due to an activation. In embodiments, the activation waveform values may be determined using any number of different statistical models, physiological models, and/or the like. According to embodiments, the calculations (e.g., models, formulas, etc.) used to determine activation waveform values may be configured to minimize dependency on amplitude. In embodiments, the calculations used to determine activation waveform values may be biased toward generating activation waveform values that are either close to (e.g., approximately) 0 or close to 1. For example, weightings, step-wise functions, discrete transforms, and/or the like may be used to bias the determination of each activation waveform value toward 0 or 1. In this manner, a plurality of sample points of an electrical signal may be represented by a plurality of activation waveform values that form an activation waveform that has an approximately discrete distribution, thereby facilitating the efficient identification of activations, even in the case of fractionated EGMs. Accordingly, embodiments may facilitate detecting activations, which may facilitate more accurate and efficient mapping, ablating, and/or the like.

In embodiments, an activation waveform value may be determined and/or further adjusted based on further analysis such as, for example, results of a consistency evaluation, as described below with reference to block 410. Any number of other types of information and/or analyses may be incorporated to refine determination of activation waveform values for each sample point of an electrical signal. In embodiments, one or more machine-learning techniques (e.g., supervised and/or unsupervised classifiers, neural networks, deep learning, artificial reasoning, etc.) may be used to modify aspects of embodiments of the method 400 such as, for example, by enhancing (e.g., making more efficient, accurate, etc.) an activation waveform value calculation formula, and/or the like.

Figure 5B:
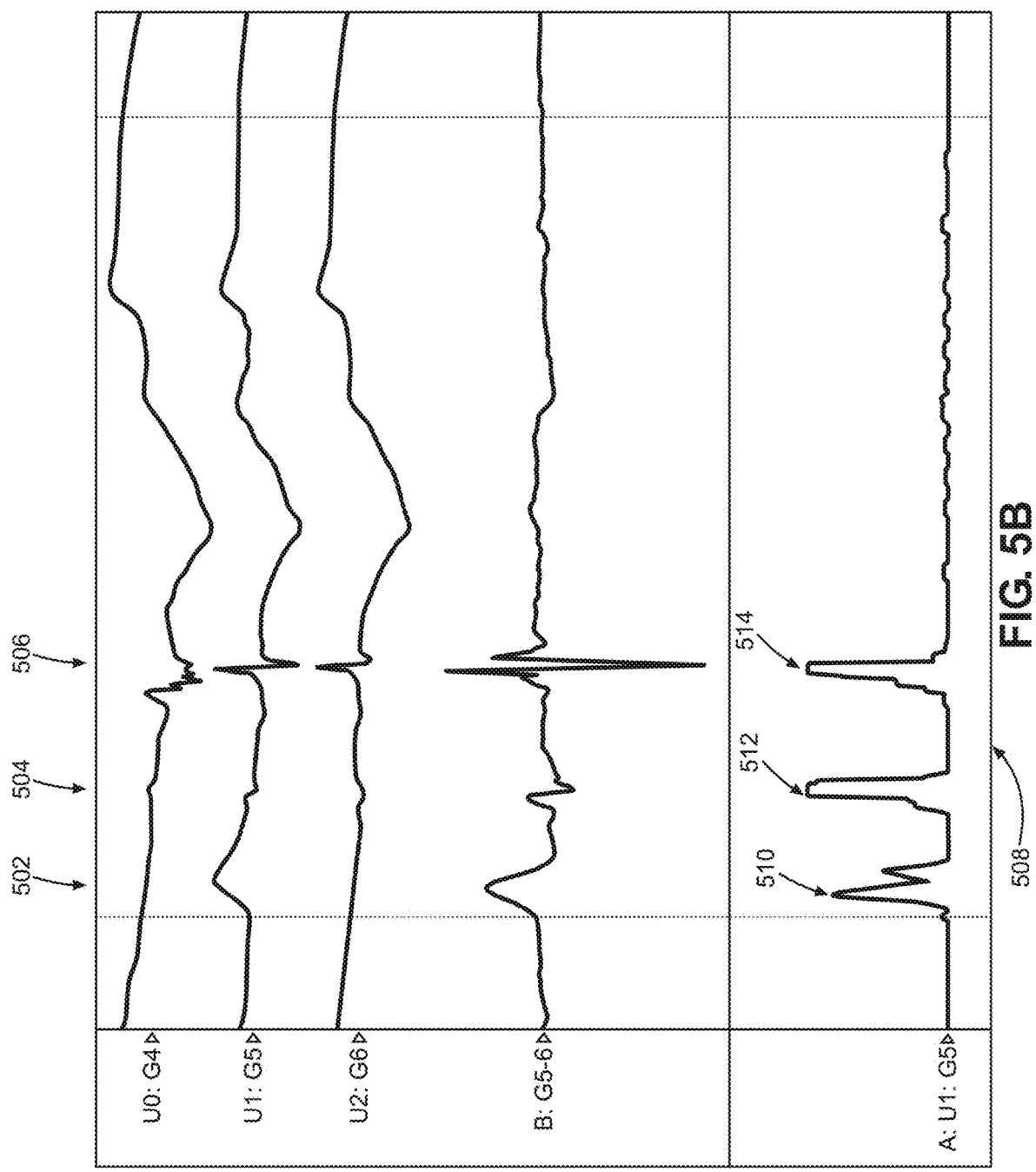
FIG. 5B depicts an activation waveform corresponding to the illustrative graphical representation of electrical signals depicted in FIG. 5A, in accordance with embodiments of the subject matter disclosed herein.

According to embodiments, identification of deflections from the baseline signal according to specified criteria may include identification of potential activations, which may be represented, for example, using an activation waveform (e.g., the annotation waveform 206 depicted in FIG. 2). For example, FIG. 5B shows an exemplary graphical representation 508 of an activation waveform A having activations 510, 512, 514, all activations detected from the electrical signal U1 received from the electrode G5 during the predetermined time period. In embodiments, the activation waveform represents identification of activations based on absolute values of deflections that deviate beyond a baseline signal according to one or more specified criteria (e.g., having an absolute value of a maximum amplitude greater than or equal to a threshold value).

As shown in FIG. 5B, a first activation 510 corresponds to a first deflection 502 detected in the signal U1, a second activation 512 corresponds to a second deflection 504 detected in the signal U1, and a third activation 514 corresponds to a third deflection 506 detected in the signal U1. As shown in FIG. 5A, the electrical signals U0, U1, U2 may be evaluated during a predetermined time period for the diagnostic assessment. As an example only, an electrical signal having multiple myocardial capture signals, each having a predetermined amplitude and a predetermined pulse width, may be evaluated to detect activations during the predetermined time period. In embodiments, the amplitude of each activation represented on the graphical representation of the activation waveform may correspond to a specified value (e.g., each activation may be assigned an amplitude of 1), an amplitude (e.g., voltage, current density, etc.) of one or more electrical signals associated with the identified activation, an aggregated amplitude value corresponding to one or more electrical signals associated with the identified activation (e.g., a mean amplitude, a median amplitude, etc.), and/or the like. In embodiments, each activation may represent a bin of an activation histogram, and the amplitude of the activation in the activation histogram may represent a relative population of the associated bin (e.g., relative to the population of one or more other bins). An activation histogram is a histogram constructed from one or more activation waveforms. Similarly, an annotation histogram is a histogram constructed from one or more annotation waveforms.

In embodiments, noise and artifact signals (e.g., deflection 502 in signal U1) may still be included in the waveform A. To remove the noise and/or artifacts, thereby creating a filtered activation waveform A, embodiments of the method 400 include performing an artifact rejection against the activation waveform based on a spatiotemporal deflection consistency between two or more electrical signals (block 410). According to embodiments, consistency may be determined in any number of different ways. For example, spatiotemporal deflection consistency between two electrical signals may refer to the occurrence of corresponding identified deflections at approximately the same time, within a specified time window, and/or the like. In embodiments, for example, a deflection that occurs in less than all of a specified set of electrical signals may be rejected as being an artifact. In embodiments, only deflections that are identified as deviating from a signal baseline according to one or more criteria are used in the consistency determination. In this manner, for example, although a first unipolar EGM may include a deflection that corresponds to a deflection identified in another EGM, the deflections may be considered to be inconsistent if the first deflection does not deviate beyond the signal baseline according to one or more signal criteria. According to embodiments, the step of evaluating deflection consistency to identify activations depicted in block 410 may be, include, be similar to, be included in, or be otherwise integrated with the step of rejecting far-field signal components depicted in block 404.

Embodiments of the artifact rejection processes described above may utilize a map and/or a grid that holds beat-gated data collected during the same rhythm. The location of the various collected signals may be used to decide whether the information in these signals should be used for artifact rejection. In embodiments, the artifact rejection may be accomplished using techniques similar to those discussed below regarding "continuous" artifact rejection. In embodiments, in contrast to the "continuous" artifact rejection, the methods discussed above may include comparing a first signal to at least a second signal that was collected at a different time than the time during which the first signal was collected. In embodiments, this may include establishing assumptions such as, for example, that the data used for artifact rejection was collected during the same rhythm, that the data used for artifact rejection was collected at the same phase of the cardiac cycle, and/or the like.

According to embodiments, a "continuous" method of assessing spatiotemporal deflection consistency to detect artifacts may be used. In embodiments of a continuous method, deviations from a baseline signals may be detected for various combinations of EGMs on a catheter (e.g., all combinations of bipolar and tripolar signals on a channel such as, e.g., tripolar signal G4-G5-G6, bipolar signal G4-G5, bipolar signal G5-G6, bipolar signal G4-G6, etc.). These baseline deviation signals may be used together to determine whether the observed deviation on any one signal is an activation or an artifact. In embodiments, this continuous method may be configured as a majority rule or voting process. In embodiments, the method may be configured as a minimum operation between the different baseline deviation signals. In embodiments, this kind of "continuous" artifact rejection compares simultaneously collected data. It does not require a cardiac map. The locations of the signals may be determined from the location relationship of the physical electrodes on the catheter.

Activations having inconsistent deflections may be removed or reduced from the activation waveform. In this way, only consistent deflections may remain in the activation waveform for examination, thereby reducing the manual examination time and costs, while facilitating the removal of noise and/or artifacts. In embodiments, for example, the plurality of electrical signals, such as the first, second, and third signals U0, U1, U2, are compared to one another and/or the activation waveform A for detecting one or more consistent deflections that are within a range of predetermined limits (e.g., minimum and maximum thresholds) relative to the signal baseline.

FIGS. 5C and 5D show the graphical representation 508 of the activation waveform A, and an illustrative graphical representation 516 of a filtered activation waveform A, having activations with only consistent deflections. In FIG. 5D, the graphical representation 516 is overlaid on top of the graphical representation 508 for easy comparison. For example, in the graphical representation 516, the first activation 510 is virtually eliminated due to inconsistency demonstrated in the signal U1. More specifically, as shown in FIG. 5, the deflection 502 of the signal U1 is inconsistent with and does not appear in other neighboring signals U0 and U2. Thus, the first activation 510 is effectively eliminated from the filtered activation waveform A. In contrast, as shown in FIG. 5, the defections 504 and 506 of the signal U1 are consistent with the deflections 504 and 506 of the neighboring signals U0 and U2. Hence, in FIG. 5D, a second activation 512 corresponding to the defection 504 and a third activation 514 corresponding to the deflection 506 remain in the filtered activation waveform A. Due to the removal of activations with inconsistent deflections, an accuracy of a cardiac map may be greatly improved.

Embodiments of the method 400 also include determining one or more activation durations (block 412), which may represent a length of an activation. That is, for example, an EGM may include a portion thereof for which all of the amplitudes deviate beyond the signal baseline according to the specified criteria. The length of the time period corresponding to that portion of the EGM may be identified as an activation duration. In embodiments, the activation waveform may be represented along a time scale, in which case, the waveform may represent the activation duration. For example, the width of the deflection in the activation waveform may represent the duration of the corresponding activation.

Embodiments of the method 400 further include aggregating the detected activations (block 414) such as, for example, by generating one or more activation waveforms, activation histograms, and/or the like. The activation waveforms and/or activation histograms may be used in facilitating presentation of the cardiac map (block 416). For example, embodiments may include annotating an electroanatomical map (e.g., a cardiac map) based on one or more annotation waveforms, annotation histograms, and/or the like. Additionally, or alternatively, the annotation waveforms and/or annotation histograms may be used in facilitating other processes such as, for example, ablation, recording information, diagnosis, and/or the like. That is, for example, in embodiments, annotation waveforms and/or annotation histograms may be used in the creation of a cardiac map (e.g., as part of a beat acceptance step such as, e.g., the beat acceptance step 308 depicted in FIG. 3), the annotation of a cardiac map (e.g., to annotate activation times), the display of a cardiac map (e.g., to facilitate a display of the spatial and/or temporal distribution of activation times), the augmenting of information (e.g., to facilitate determining and/or highlighting (e.g., emphasizing computationally and/or visually) characteristics of EGMs (which may be displayed) and/or EGMs having certain characteristics), an ablation procedure (e.g., to detect activations, distinguish between activations and artifacts, etc.), and/or the like. For example, in embodiments, annotation waveforms and/or annotation histograms may be used to facilitate quantification of specific EGM characteristics (e.g., by using activation waveforms to determine metrics such as, e.g., a portion of time during which a channel was active (activation duration), etc.).

In embodiments, a cardiac map may be generated and/or annotated based, at least in part, on the cardiac electrical signal features and/or the activation waveform (which may also be a cardiac electrical signal feature). In embodiments, the cardiac map may also be generated and/or annotated, at least in part, using any number of other signals, techniques, and/or the like. For example, embodiments may utilize impedance mapping techniques to generate and/or annotate one or more portions of the cardiac map such as, for example, an anatomical shell upon which electrical signal features are represented. In embodiments, a surface may be fitted on one or more of the points associated with the cardiac electrical signals to generate a shell representing the endocardial surface of the one or more cardiac structures. In embodiments, a surface may also be fitted on one or more of the points associated with the cardiac electrical signals to generate a shell representing an epicardium surface or other excitable cardiac tissue. In embodiments, one or more of the cardiac electrical signal features at the corresponding points can be included on the shell to generate a cardiac map of the one or more cardiac structures. For example, embodiments may include displaying annotations on the cardiac map that represent features, extracted from the cardiac electrical signals and/or derived from other features, such as, for example, activation times, minimum voltage values, maximum voltages values, maximum negative time-derivatives of voltages, instantaneous potentials, voltage amplitudes, dominant frequencies, peak-to-peak voltages, and/or the like.

Cardiac electrical signal features may be represented on the cardiac map and may be, or include, any features extracted from one or more corresponding sensed cardiac electrical signals and/or derived from one or more of such features. For example, a cardiac electrical signal feature may be represented by a color, such that if the cardiac electrical signal feature has an amplitude or other value within a first range then the cardiac electrical signal feature may be represented by a first color, whereas if the cardiac electrical signal feature has an amplitude or other value that is within a second range that is different than the first range, the cardiac electrical may be represented by a second color. As another example, the cardiac electrical signal feature may be represented by a number (e.g., a 0.2 mV sensed cardiac electrical signal feature can be represented by a 0.2 at its respective position on the surface map). Examples of a cardiac electrical signal feature that can be represented at the first surface point include, but are not limited to, an activation, an activation time, an activation duration, an activation waveform, a filtered activation waveform, an activation waveform characteristic, a filtered activation waveform characteristic, a minimum voltage value, a maximum voltages value, a maximum negative time-derivative of voltage, an instantaneous potential, a voltage amplitude, a dominant frequency, a peak-to-peak voltage, and/or the like.

In embodiments, other features such as, for example, non-electrical signal features, non-cardiac electrical signal features, and/or the like, can be represented on an anatomical map at respective locations. Examples of non-electrical signal features include, but are not limited to, features derived from magnetic resonance imaging, a computerized tomography scan, ultrasonic imaging, and/or the like.

According to embodiments, activation waveforms, as described above, may be useful for facilitating any number of different functionalities. For example, in embodiments, activation waveforms may be used to generate activation maps that more clearly represent activation propagation. In embodiments, activation waveforms may facilitate automatic classification of electrical signals such as EGMs. Activation waveforms may be used to facilitate cardiac mapping tools such as, for example, tools that facilitate accurate interpretation of activation maps. For example, embodiments facilitate generating activation histograms representing classifications associated with amounts of tissue activating at each activation time within a specified time period. Activation histogram waveforms may be presented on a display device, and may be associated with a cardiac map. Activation histogram waveforms may facilitate identifying and focusing on certain cardiac events, small tissue regions with activation times satisfying a certain set of criteria, and/or the like. Similarly, local activation histograms may facilitate map interpretation and navigation by representing aggregated activity across smaller regions of tissue.

According to embodiments, activation waveforms, as described above, may be useful for facilitating any number of different functionalities. For example, in embodiments, activation waveforms may be used to generate activation maps that more clearly represent activation wavefront propagation by representing activation waveform propagation. In embodiments, activation waveforms may facilitate automatic classification of electrical signals such as EGMs. Activation waveforms may be used to facilitate cardiac mapping tools such as, for example, tools that facilitate accurate interpretation of activation maps. For example, embodiments facilitate generating activation histograms representing classifications associated with amounts of tissue activating at each activation time within a specified time period. Activation histogram waveforms may be presented on a display device, and may be associated with a cardiac map. Activation histogram waveforms may facilitate identifying and focusing on certain cardiac events, small tissue regions with activation times satisfying a certain set of criteria, and/or the like. Similarly, local activation histograms may facilitate map interpretation and navigation by representing aggregated activity across smaller regions of tissue.

Annotation Histogram

Understanding electroanatomical activation maps is often difficult, particularly in cases associated with certain patient populations such as, for example, those having atrial and/or ventricular tachycardia, atrial fibrillation, and/or the like. Accurate interpretation of activation maps typically involves following multiple wavefronts propagating over a complex 3D surface. As such, map interpretation largely remains a manual process, highly dependent on user skill. Poor map interpretation may lead to ineffective therapy, misdiagnosis, and/or the like.

According to embodiments, a processing unit (e.g., by a processing unit such as the processing unit 120 depicted in FIG. 1 and/or the processing unit 200 depicted in FIG. 2) may be configured to construct an activation histogram that represents a distribution of activation information such as, for example, the incidence rate of activations within a mapping window, the surface area of tissue associated with activations within a mapping window, and/or the like. In embodiments, for example, the activation histogram includes a number of histogram bins, each of the histogram bins corresponding to a time period (e.g., an activation duration, an activation time, a mapping window, etc.), an activation region, and/or the like. In embodiments, the activation histogram includes all periods of activation for each EGM in the map. The histogram may be normalized to avoid bias due to non-uniform spatial sampling of EGMs. The resulting histogram may facilitate finding critical regions of interest, thereby assisting with map interpretation.

According to embodiments, an activation histogram may be generated at least partially based on one or more activation waveforms, one or more activation maps, activation information, and/or the like. In embodiments, a processing unit may be configured to instantiate a histogram generator such as, for example, the histogram generator 216 depicted in FIG. 2. The histogram generator may include, for example, computer-executable instructions configured to cause a processor (e.g., the processor 202 depicted in FIG. 2) to generate activation histograms corresponding to activation waveforms, activation maps, activation information, and/or the like. The histogram generator may be configured to generate any number of different activation histograms associated with any number of different activation waveforms, activation maps, activation information, and/or the like.

According to embodiments, and as indicated above, a histogram generator may be configured to generate an activation histogram at least partially based on an activation map. In embodiments, an activation map may be generated by annotating an anatomical shell with indications of activations. For example, in embodiments, an anatomical shell may be generated using a three-dimensional mesh, and a mapping engine may be configured to annotate the shell with activation information by associating activation information (e.g. activation times) with vertices of the mesh. In embodiments, the mapping engine may select one activation time out of a set of activation times (or generate a mapping value based on the set of activation times) that correspond, spatially, to a given vertex of the mesh. A mapping engine may be configured, for example, to perform aspects of embodiments of the methods of facilitating display of cardiac mapping information, as described in U.S. application Ser. No. 15/230,233, entitled "CARDIAC MAPPING USING A 3D GRID," filed on Aug. 5, 2016, the entirety of which is incorporated herein by reference for all purposes. Similarly, embodiments of the system 100 depicted in FIG. 1 and/or the processing unit 200 depicted in FIG. 2 may be, include, be similar to, or be included in the system 100 depicted in FIG. 1, and/or the processing unit 200 depicted in FIG. 2 of U.S. application Ser. No. 15/230,233, incorporated above.

In embodiments, to generate an activation histogram based on the activation map, a histogram generator (e.g., the histogram generator 216 depicted in FIG. 2) may be configured to bin annotated surface area associated with each vertex in bins that, for example, correspond to vertices, activation times, activation locations, regions (e.g., defined using a stochastic radius), and/or the like. In embodiments, for example, a processing unit may be configured to determine the percentage of the mesh that has been colored to indicate activation time by summing surface areas of annotated portions of the mesh, as represented in an activation histogram. In embodiments, an activation histogram may be generated based on electrode timings. For example, a histogram generator may be configured to bin annotated surface area based on electrodes. In embodiments, the histogram generator may be configured to utilize density normalization when generating the activation histogram, and may, in embodiments, use weighting (e.g., similar weighting to that used in creating activation waveforms, in embodiments— that is, for example, similar biased probability calculations and/or the like may be utilized in generating the activation histograms). In embodiments, an activation histogram may be generated such that, for example, one or more electrodes contribute to multiple bins, each electrode contributes to one bin (e.g., which may be used, e.g., for generating an activation histogram based on activation times), and/or the like.

For example, in embodiments, because an activation map generated as described above represents only one activation time for each vertex (and, in embodiments, interpolated values represented between vertices), some activation maps may not represent true patterns of activation. For example, in embodiments, the mapping value (e.g., represented activation time) selection process may miss important information (e.g., associated with other, non-selected, activation times within a neighborhood (e.g., a stochastic radius) of one or more grid nodes associated with a given vertex). In embodiments, for example, a selection process may represent an identified activation time, but may not represent multiple activations corresponding to the location represented by the vertex, in which case the activation map may not accurately represent the amount (e.g., the surface area) of tissue activating at a given time (or within a given time window).

Embodiments include using a combination of activation histograms and activation waveforms for detecting inaccuracy in an activation map. That is, for example, a histogram generator may be configured to generate an activation histogram based on the activation map, as described above. Because the activation histogram is generated using the mapped activation values, it will include the same inaccuracy (e.g., an over-generalization of important information, missing information, etc.). An activation waveform generator may generate an activation waveform based on the same set of signals used to generate and/or annotate the map, and a processing unit may be configured to compare a histogram generated from the activation waveforms and a histogram generated from the mapped values. Through the comparison, the processing unit may determine that the histogram generated from the mapped activation values, and thus, the map, includes the inaccuracy. In embodiments, a notification may be presented to a user that the inaccuracy has been detected.

In embodiments, the mapping engine may be configured to annotate the map with supplemental annotations corresponding to the activation information associated with the inaccuracy. For example, the mapping engine may be configured to annotate the map with representations of each of a number of identified activation times, which may be determined based on the activation waveform. In this manner, embodiments may facilitate enhancing the accuracy of activation maps without expending the processing resources that would typically be required to annotate the map by re-analyzing the EGMs and/or features extracted therefrom.

Embodiments may be used, for example, to determine an amount of surface area of tissue activating at a certain time (or during a certain time window) in a situation in which one or more of the corresponding EGMs is, for example, a long, fractionated EGM.

Aspects of embodiments of the methods described above for generating and/or using activation histograms may be used for generating and/or using histograms corresponding to any number of different types of annotations (referred to, generally, herein as "annotation histograms"). Annotations may include, for example, instantaneous potential, activation time, presence of fractionation, voltage amplitude, spectral content, dominant frequency and/or other properties of an electrical signal or signals. In embodiments, for example, annotation histograms may be used to determine percentage of surface area of a map that has a certain range of annotation values (e.g., a certain voltage range, etc.). In embodiments, a representation of an annotation histogram may be presented to a clinician to facilitate exploration of the cardiac information. For example, in embodiments, a voltage histogram may be presented and include interactive GUI features that enable a clinician to dynamically explore whether there are certain voltages corresponding to larger amounts of annotated surface area, and/or the like. For example, in embodiments, a representation of an annotation histogram may include selectable representations of bins such that, for example, upon receiving an indication of a user selection of one or more bins, the processing unit is configured to highlight the corresponding surface area of the annotated map, to present a numerical representation of the corresponding surface area of the annotated map, and/or the like.

In embodiments, the processing unit may be configured to facilitate a discrete representation of a histogram and/or a continuous representation of a histogram. For example, a discrete representation may include a representation of individual bins, while a continuous representation may include a waveform (e.g., curve). In embodiments, the processing unit may be configured to determine whether to facilitate presentation of a representation of a discrete histogram or a continuous histogram based on number of values included in one or more of the bins of the annotation histogram. For example, in embodiments, the processing unit may determine whether one or more of the histogram bins (e.g., the histogram bin with the most members) includes a number of members exceeding a threshold. If the number of members of the one or more specified bins exceeds the threshold, the processing device may facilitate presentation of a continuous representation of the histogram, whereas, if the number of members does not exceed the threshold, the processing device may facilitate presentation of a discrete representation of the histogram. According to embodiments, any number of different considerations, algorithms, user inputs, and/or the like, may be incorporated into any number of different decisions regarding presentation of a representation of a histogram.

Aspects of embodiments of the techniques described herein for generating and/or using annotation maps may facilitate patient categorization, which may be used in triaging processes, billing processes, insurance risk prediction processes, prognosis determination, and/or the like. In embodiments, for example, annotation histograms may be used to characterize a cardiac map by facilitating an identification of each portion of the map that has a certain characterization, as determined, for example, based on annotation histograms. For example, embodiments may facilitate identifying which EGMs are fractionated, duration of fractionation, other characteristics that may be correlated to the fractionation, and/or the like. In embodiments, a GUI of a mapping system may provide a surface area determination tool, which may utilize annotation histograms, as described herein, to determine surface area associated with one or more characteristics selected by a user, or otherwise provided to the processing unit as user input. In embodiments, annotation histograms may be generated, but not represented in a display (e.g., annotation histograms may be useful for any number of different types of analyses, including, for example, aspects of embodiments of those described herein, analyses not described herein, and/or combinations of these).

According to embodiments, as indicated above, a histogram generator may be configured to generate an activation histogram at least partially based on an activation waveform. In embodiments, activation histograms based on activation waveforms may include any number of different features described herein with respect to activation histograms generated from activation maps (and, generally, annotation histograms, as described herein). In embodiments, the histogram generator may be configured to generate an activation histogram by receiving an activation waveform for each EGM in a particular map, approximating a local density of activations for each EGM in the map. The local density of activations may be based on an activation region. In embodiments, a mapping engine (e.g., the mapping engine 220 depicted in FIG. 2) may be configured to cause a display device to display a histogram waveform. In embodiments, the amplitude of the histogram waveform represents the density or relative population of the corresponding bin. For example, in embodiments, the activation waveform includes activations identified based on an aggregation of a number of EGMs. The activation histogram may be configured such that the relative population of each bin is based on the contribution of EGMs within a selected region to the activation represented at the corresponding time. That is, for example, an activation histogram may represent the amount and/or location of tissue activating at each time within a mapping window. In this manner, for example, a user may identify a slow channel by looking for minimums on a waveform representation of the activation histogram.

The histogram generator may be configured to facilitate presentation of a GUI that enables a user to modify one or more criteria used for generating, interpreting, and/or representing an activation histogram. The GUI may be configured to highlight regions of an electroanatomical map in response to user selection of a portion of a representation of an activation histogram. In this manner, embodiments of the histogram waveform may represent the relative contributions of activations from certain regions or time periods on activation propagation. According to embodiments, the activation histograms may be used to facilitate highlighting regions of interest on a map.

Any number of different methods for highlighting regions corresponding to a selected bin or bins of an activation histogram may be employed in embodiments. Selection of the bin or bins may be achieved, for example, by selection using a user input device, of a portion of a representation of a histogram waveform. For example, for a selected histogram bin, the processing unit may be configured to identify EGMs in the map associated with that selected histogram bin. In response to identifying the EGMs corresponding to a selected histogram bin or bins, the processing unit may be configured to cause the region of the map associated with the identified EGMs may be emphasized. In embodiments, regions of the map may be emphasized by highlighting them (e.g., adding a highlighting color), changing colors associated with the regions, changing a display parameter (e.g., contrast, brightness, white-balance, etc.) associated with the regions, and/or the like.

According to embodiments, a GUI used for presenting the map may include any number of different input tools for manipulating the map. For example, the GUI may include a play/pause button, a tool configured to facilitate manual selection of the histogram bin or bins, tools configured to facilitate manual adjustment of parameters (e.g., signal baseline definitions, thresholds, EGM characteristics, filters, etc.), and/or the like. In embodiments, for example, the GUI may include a selection tool that can facilitate refining selections of highlighted EGMs, select particular EGMs and/or activations, and/or the like.

According to embodiments, activation histograms may be used to facilitate finding and highlighting small regions on a map with activation times relevant to a certain arrhythmia, activation circuit, and/or the like, with less computational burden than conventional region of interest features. As an example, many atrial and ventricular tachycardias arise because of slow conduction through a narrow channel such as an isthmus. This leads to a self-sustaining reentrant activation pattern. Often, the isthmus is activating when most of the rest of chamber is not activating, but due to the imprecise nature of the aggregations used for generating conventional maps, it is difficult for the user to see this activation.

Figure 6A:
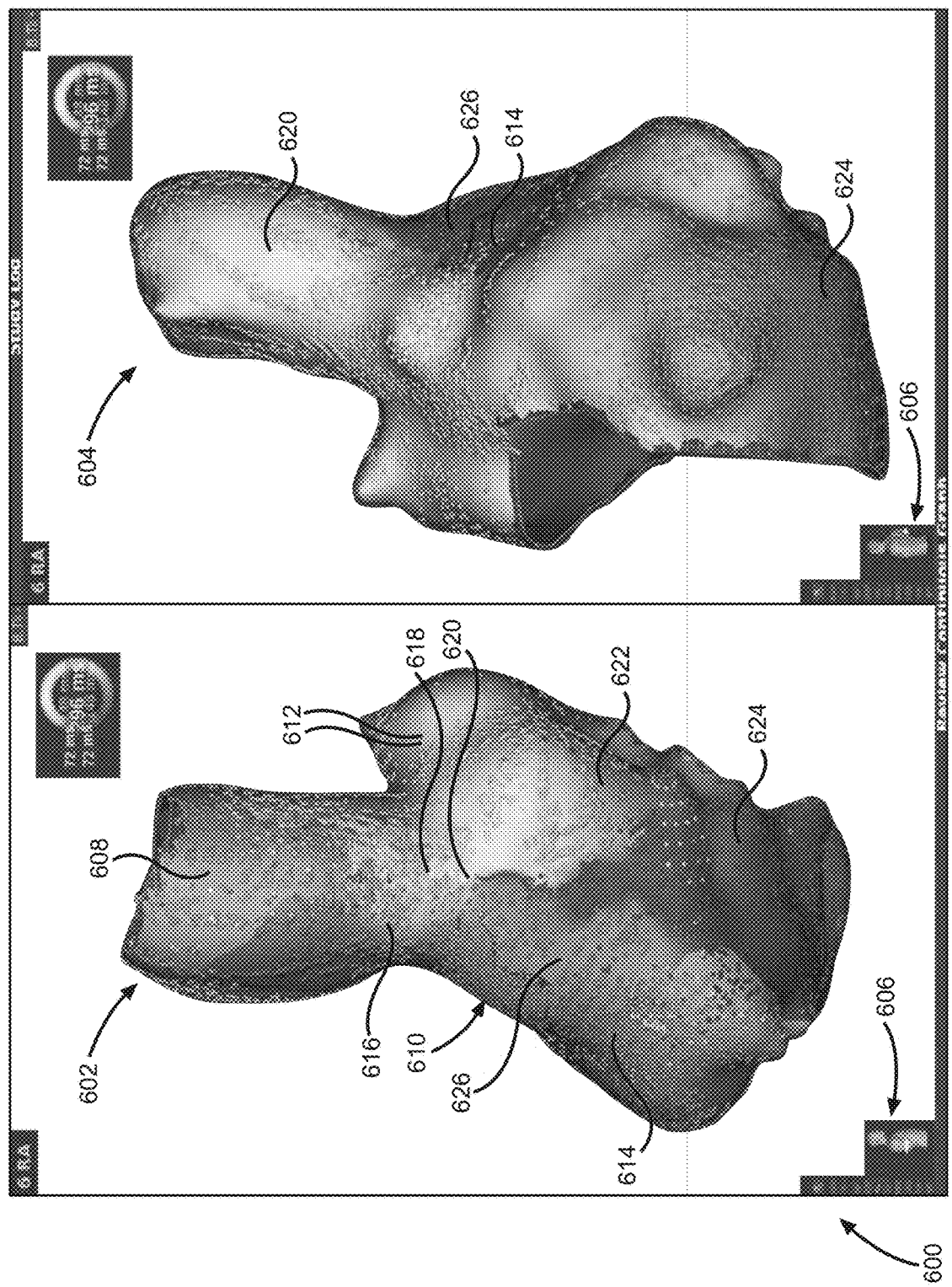
FIG. 6A depicts an illustrative screenshot from an interactive graphical user interface (GUI) presented using a display device associated with a cardiac mapping system, showing views of an illustrative cardiac map, in accordance with embodiments of the subject matter disclosed herein.

FIG. 6A depicts an illustrative screenshot from an interactive graphical user interface (GUI) 600 presented using a display device associated with a cardiac mapping system, showing views of an illustrative cardiac map, in accordance with embodiments of the subject matter disclosed herein. According to embodiments, the cardiac mapping system may be, be similar to, include similar features as, include, or be included within the mapping system 100 depicted in FIG. 1. The GUI 600 includes a first view 602 of the cardiac map and a second view 604 of the cardiac map. As shown, the first view 602 and the second view 604 represent two different orientations of the same cardiac map. In embodiments, the GUI 600 may be configured to present only one view of the cardiac map at a time. In embodiments, the GUI 600 may be configured to present, simultaneously, sequentially, and/or alternatively, any number of different views of any number of cardiac maps. In embodiments, for example, the GUI 600 may be configured to present a first cardiac map having annotations representing activations and a second cardiac map having annotations representing electrical potential, current density, and/or the like. As shown, an orientation indicator 606 may be configured to indicate the orientation, with respect to the body housing the heart, of the cardiac map that corresponds to the particular view 602, 604.

As shown in FIG. 6A, the cardiac map includes an anatomical shell 608 and annotations 610 displayed on the anatomical shell 608. In embodiments, the map may be an activation map, on which activation locations are indicated by raised bumps 612 and activation timing may be represented using colors 614, 616, 618, 620, 622, 624, and 626. That is, for example, in the illustrated embodiments, different colors represent different durations of time relative to the last activation detected at a reference location. In embodiments, the raised bumps 612 may be configured to represent a location associated with an acquired electrical signal (e.g., an EGM), a virtual location associated with an aggregation of acquired electrical signals, and/or the like. As shown, the GUI 600 may also include a legend 628 configured to indicate the values represented by the annotation colors 614, 616, 618, 620, 622, 624, and 626.

In embodiments, as an activation wavefront propagates through the cardiac structure, the color annotation associated with each region of the heart changes in response to algorithms configured to estimate, for each region, an amount of time between activation in the region and activation at a reference location. However, the nature of the larger swaths of color changing from one color to another without any clear boundaries can make such activation maps difficult to interpret. As such, embodiments facilitate presenting, on a cardiac map, an emphasized representation of a region of interest.

Figure 6B:
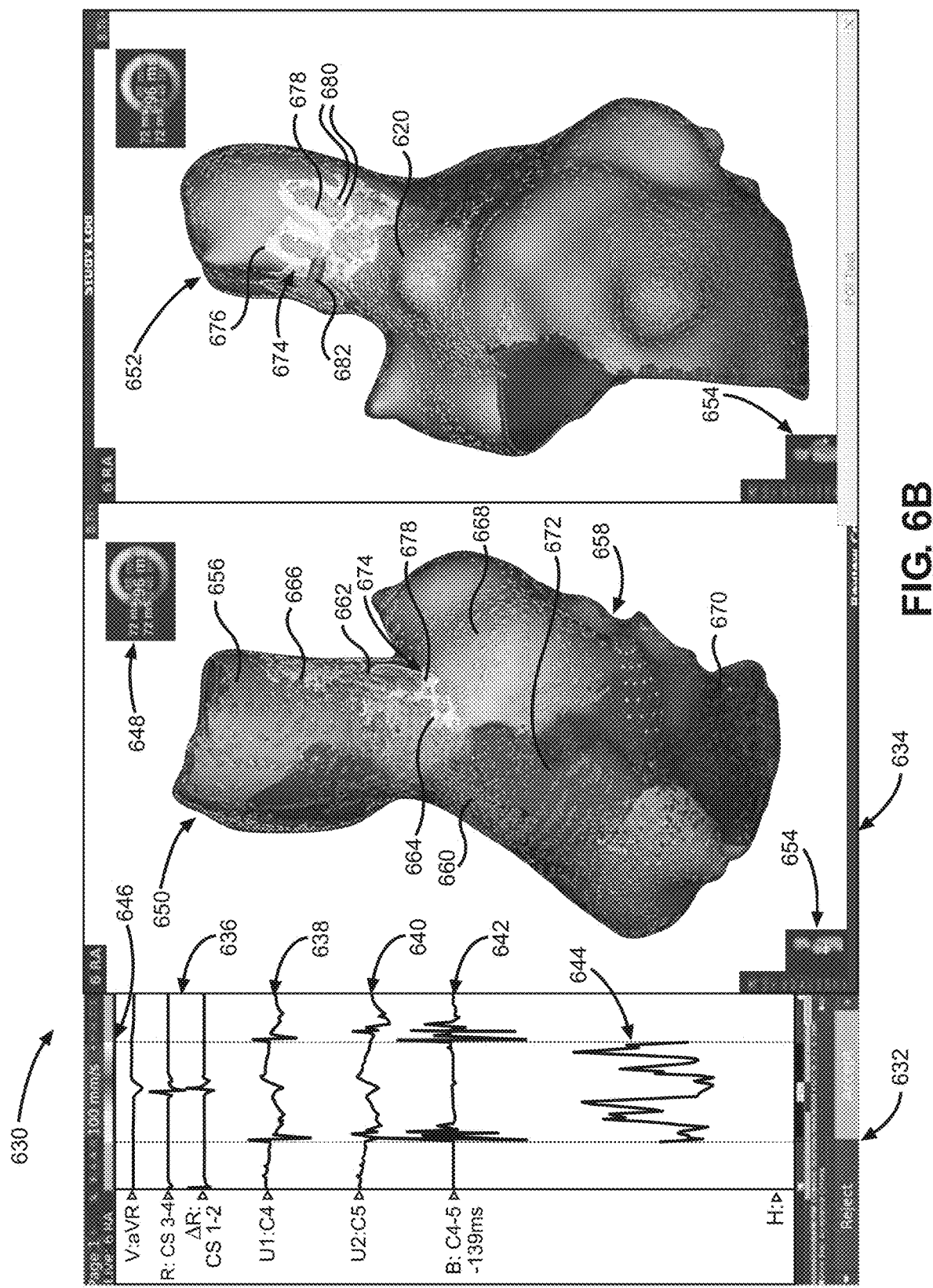
FIG. 6B depicts an illustrative screenshot from an interactive graphical user interface (GUI) presented using a display device associated with a cardiac mapping system, showing views of an illustrative cardiac map, in accordance with embodiments of the subject matter disclosed herein.

FIG. 6B depicts an illustrative screenshot from an interactive graphical user interface (GUI) 630 presented using a display device associated with a cardiac mapping system, showing views of an illustrative cardiac map, in accordance with embodiments of the subject matter disclosed herein. According to embodiments, the cardiac mapping system may be, be similar to, include similar features as, include, or be included within the mapping system 100 depicted in FIG. 1. The GUI 630 may be, be similar to, include similar features as, include, or be included within the GUI 600 depicted in FIG. 6. FIG. 6B includes a first screen region 632 and a second screen region 634.

The first screen region includes a stacked display of representations of cardiac electrical signal features such as, for example, beat metrics 636; EGM waveforms 638, 640, and 642; and a representation 644 of an activation histogram. The signal features 636, 638, 640, 642, and 644 may all be aligned along a time scale. A color legend 646 may associate annotation colors on the map with the corresponding portions of the signal features 636, 638, 640, 642, and 644, and may be coordinated with another color legend 648 (shown as being presented in the second screen region 634) configured to associate the annotation colors with specific values (e.g., time period durations).

The second screen region 634 depicts a first view 650 and a second view 652 of cardiac map. As shown, the first view 650 and the second view 652 represent two different orientations of the same cardiac map. In embodiments, the GUI 630 may be configured to present only one view of the cardiac map at a time. In embodiments, the GUI 630 may be configured to present, simultaneously, sequentially, and/or alternatively, any number of different views of any number of cardiac maps. In embodiments, for example, the GUI 630 may be configured to present a first cardiac map having annotations representing activations and a second cardiac map having annotations representing electrical potential, current density, and/or the like. As shown, an orientation indicator 654 may be configured to indicate the orientation, with respect to the body housing the heart, of the cardiac map that corresponds to the particular view 650, 652.

As shown in FIG. 6B, the cardiac map includes an anatomical shell 656 and annotations 658 displayed on the anatomical shell 656. In embodiments, the annotations 658 may represent any number of different metrics such as, for example, activations, voltages, impedance values, propagation velocity, current density, and/or the like. In embodiments, as in FIG. 6A, the map may be an activation map, on which activations are indicated using a first set of colors 660, 662, 664, 666, 668, 670, and 672. Although seven distinct colors are discussed herein, any number of colors may be used for such representations. In embodiments, in addition to, or in lieu of, colors, other representations may be used to represent activations such as, for example, textures, location markers, curves, vectors, and/or the like.

According to embodiments, the histogram waveform 644 may be a selectable GUI element such that, for example, a user can move a cursor over a portion of the histogram waveform 644 and select the portion of the histogram waveform 644 to which the cursor points, for example, by pressing a mouse button, tapping a touchscreen, and/or the like. In embodiments, in response to receiving an indication of the user selection of a portion of the histogram waveform, the processing unit may cause a corresponding region (referred to herein as the "selected region") of the map 650, 652 to be emphasized. The processing unit may cause the display device to present a representation 674 of the selected region.

The representation 674 of the selected region may be configured to emphasize the selected region. In embodiments, for example, the representation 674 of the selected region may be distinguished from adjacent regions of the map by being highlighted. That is, for example, the representation 674 of the selected region may be a highlighting of the selected region of the map (e.g., by making the representations of the electrical signal features in the selected region 674 brighter, a different color, etc.). As shown, the representation 674 of the selected region may include a border 676 surrounding an internal region 678. The internal region 678 may represent a portion of the selected region (as may, in embodiments, the border 676). In embodiments, the border 676 and/or the internal region 678 may be rendered using display features that differentiate the representation 674 of the selected region from adjacent regions of the map. In embodiments, for example, the border 676 and/or the internal region 678 may have a color or colors that are different than the color or colors of adjacent regions, the border 676 and/or the internal region 678 may have a display parameter value that differs from the values of the same display parameter associated with adjacent regions of the map, and/or the like. In embodiments, individual activation locations may be indicated using representations 680 such as "Xs," raised bumps, and/or the like.

In embodiments, the processing unit may also be configured to cause the display device to display a virtual probe 682. A virtual probe 682 may be used to inspect any of the cardiac electrical signal features and/or the corresponding cardiac electrical signals that were sensed by a mapping probe. To do so, the processing unit may be configured to position the virtual probe 682 at one or more different positions on the cardiac map, in response to receiving a user input. Examples of user input that may be indicative of positioning the virtual probe 682 at a position include, but are not limited to, a single or double mouse click, a touch on a touchscreen, hovering a cursor over the selection location, and/or the like. After the virtual probe 682 is at a position, the processing unit may be configured to reposition the virtual probe 682 to a different position on the cardiac map and/or the surface map, in response to receiving a user input. Examples of user input that may be indicative of repositioning the virtual probe 682 to a different position include, but are not limited to, a mouse click and drag on the virtual probe and/or a touch and drag on the virtual probe. In embodiments, the processing unit may be configured to place the virtual probe 682 at a location that corresponds to the selected portion of the histogram waveform. In embodiments, the processing unit may be configured to cause the display device to present the portion of the histogram waveform corresponding to the location at which a user places the virtual probe 682 on the cardiac map.

In embodiments, GUI 632 may facilitate displaying EGMs 638, 640, and 642, and/or features of cardiac electrical signals that were sensed at positions that are within a threshold distance of the position of the virtual probe's tip. Examples of electrical signals that may be displayed include, but are not limited to, a graph of the EGM waveform (which may include both bipolar and constituent unipolar EGMs) that was sensed by the mapping probe at a position closest to the position of the virtual probe's tip (referred to hereafter as "distal EGM"), graphs of other EGMs sensed by the mapping probe (referred to hereafter as "proximal EGMs") that are associated with the same beat as the beat associated with the distal EGM, activation times of the distal and proximal EGMs, and fractionation indexes of the distal and proximal EGMs.

According to embodiments, for example, the GUI 630 may be configured to receive, from a user input device, a selection of a region of the cardiac map. The user input device used to make the selection may include a mouse, a touchscreen and/or the like, that is used to manipulate a selection tool that is provided on the GUI 632 provided by the display device. The selection tool may include, for example, a brush, a cursor for enclosing the selected region by drawing a freeform shape around the region, an expandable polygon selection tool, a virtual probe 682, and/or the like, and may be, in embodiments, selected from a number of optional selection tools. In embodiments, the selection tool may have an adjustable size, behavior and/or other characteristics thereof. In this manner, for example, a user may select a desired selection tool and a size thereof. Selecting a region of the map may include, for example, circling the region of the map using a mouse or touchscreen device to manipulate a cursor, brushing over the region of the map using an input device to manipulate a brush, and/or the like.

According to embodiments, activation (and/or other annotation) histograms may be used for any number of different types of analyses. In embodiments, for example, activation histograms may be used to more clearly represent information associated with a selected region of a cardiac map. For example, finding and showing small regions with activation times critical to sustaining the circuit will guide and help validate map interpretation in many cases. In embodiments, for instance, a histogram of the amount of tissue activating at each time within a tachycardia cycle length will often have a minimum that corresponds to the critical isthmus. In this manner, for reentrant tachycardias, for example, selecting a minimum in the histogram waveform may cause the processing unit to highlight a critical isthmus (and/or other relevant regions) in the map. When more than one region is highlighted, map context may still useful in determining the critical isthmus. In another example, for focal tachycardias, selecting the portion of the histogram waveform just before the bulk of the histogram will highlight the focal site. According to embodiments, any number of different regions may be highlighted for any number of different reasons, to diagnose and/or monitor any number of different types of arrhythmia, and/or the like.

In embodiments, annotation histograms may be used to facilitate providing a surface area determining tool. For example, a GUI may provide a representation of a caliper that a user may position over a particular portion of a representation of an annotation histogram to determine the percentage of tissue corresponding to that portion of the annotation histogram (e.g., to determine a surface area of tissue activating within a time period associated with the selection based on the caliper location).

Local Annotation Histogram

In embodiments, annotation waveforms and annotation histograms may be used to facilitate map interpretation in any number of different situations. For example, embodiments may facilitate map interpretation for use during an ablation procedure. Map interpretation for ablation guiding typically involves a steep learning curve, leading to an adoption and usage barrier. For example, map interpretation for gap finding in ablations lines, tachycardia isthmus detection, tachycardia focus detection, and/or the like, is often challenging. While full maps work well as a macroscopic indicator of cardiac conditions, they are typically not accurate and precise enough to be used for guiding some ablation procedures. Also, using EGM-by-EGM analysis to guide ablation is computationally and time intensive due to the high densities of EGMs acquired during mapping. Accordingly, a localized regional representation of relevant information may be desirable.

Embodiments include a dynamic regional review GUI tool. The regional review tool may be implemented, for example, as a program component stored in a memory (e.g., the memory 204 depicted in FIG. 2) and executable by a processor (e.g., the processor 202 depicted in FIG. 2). In embodiments, the regional review tool may be integrated with one or more other program components, tools, plug-ins, applications, and/or the like. The regional review tool may be configured to present an easy-to-read aggregated "activity snapshot" across a target patch of tissue. In embodiments, the activity snapshot may be, for example, a representation of an aggregation of one or more activation waveforms and/or a representation of an activation histogram. In this manner, the tool leverages the detection and artifact rejection algorithms used to generate an efficient and relevant activation waveform to only show real activity in a simple waveform that can be quickly interpreted by a user.

According to embodiments, for example, the GUI may include a selection tool such as, for example, a virtual probe, as described above with reference to FIG. 6B. In embodiments, the selection tool may be or include a cursor (pointer) tool, a lasso tool, an expandable box tool, and/or the like. The selection tool may include a cursor that can be manipulated to be positioned over a region of interest of a cardiac map. Upon receiving an indication that a region of the map has been selected ("the selected region"), a processing unit (e.g., the processing unit 120 depicted in FIG. 1 and/or the processing unit 200 depicted in FIG. 2) may generate a local activation waveform, and/or a local activation histogram, corresponding to the selected region. The processing unit may cause the display device to present a representation of the local activation waveform or a representation of the local activation histogram (e.g., a local histogram waveform). The user may quickly assess the activation activity in the selected region and may move the virtual probe to do the same in any other region of the map.

For example, FIG. 7A depicts a portion of a GUI 700 that is presenting unipolar EGMs 702 and 704, and bipolar EGM 706, in accordance with embodiments of the subject matter disclosed herein. In many instances, it may be desirable to quickly ascertain the activations in the EGMs 702, 704, 706. In embodiments, a processing unit (e.g., the processing unit 120 depicted in FIG. 1 and/or the processing unit 200 depicted in FIG. 2) may be configured to receive user input; generate, in response to the user input, an activation waveform associated with the EGMs 702, 704, and 706; and present a representation 708 of the activation waveform on the GUI 700. For example, the user input may include an indication of a request for generation of an activation waveform and an indication of a selected window 710. A user the select the window 710 using a user input device such as, for example, a mouse, a touchscreen, and/or the like. In embodiments, the representation 708 of the activation waveform facilitates rapid identification of activations 712, which may facilitate more rapid and accurate understanding of activation information associated with a cardiac map. According to embodiments, a representation of an activation histogram corresponding to the activation waveform may be presented in addition to, or in lieu of, the representation of the activation waveform, and may be configured to represent amounts and/or locations of tissue activating at each sampled time point during a cardiac cycle.

To explain embodiments of the regional review tool, the following discussion is presented in the context of an illustrative use case; however, it should be readily understood by those having skill in the relevant arts that the technology described in the context of this use case may be applied in any number of different types of situations, with any number of other technologies, and in the context of any number of different use cases. FIG. 8 depicts a portion of a cardiac map 800 rendered by a processing unit using a display device, in accordance with embodiments of the subject matter disclosed herein. During some ablation procedures, the objective is to burn a line 802 of tissue (a "block") between two tissue regions 804 and 806 to prevent an activation wavefront from crossing from the first tissue region 804 into the second tissue region 806, to keep an activation in the first tissue region 804 from affecting an activation in the second tissue region 806, and/or the like.

To assess the effectiveness of the ablation, the user may wish to inspect the line 802 to determine whether there are any gaps in the line 802. In this context, gaps are areas where activation is propagating across the line 802 from the first tissue region 804 to the second tissue region 806, or where an activation in the first tissue region 804 otherwise affects an activation in the second tissue region 806. This is not generally clear from a review of a cardiac map 800, which includes colored regions generated using aggregation and interpolation of large amounts of data, and inspecting each of the great many representations 808 of individual EGMs would be time consuming. Additionally, abnormalities 810 may be introduced by far-field interference, which may be misleading to the user.

According to embodiments, gaps in ablation lines can be readily identified using a simple representation of local activity such as, for example, a representation of a local activation waveform or a local activation histogram, as described herein. Accordingly, in embodiments, a regional review tool (e.g., the regional review tool described above with reference to FIGS. 6A and 6B) may be provided via a GUI that enables a user to view a representation of activation activity information associated with a selected region.

FIGS. 9A-9E depict illustrative sequential instances of a first portion 900 and a second portion 902 of a GUI, including a portion 904 of a cardiac map and a representation 906 of an activation histogram, respectively, in accordance with embodiments of the subject matter disclosed herein. As used herein, an "instance" of an anatomical map (e.g., a cardiac map) refers to the anatomical map corresponding to a certain point in time. Thus, for example, a first instance of the cardiac map may present information associated with a first time and a second instance of the cardiac map may present information associated with a second time, the second time being later in time than the first time. The first and second portions 902 and 904 are shown in FIGS. 9A-9E as disjoined—that is, the first and second portions 902 and 904 are not shown in necessarily the same orientation they might have on a GUI 900. In embodiments, the first and second portions 902 and 904 of the GUI may be arranged according to any number of different orientations.

As shown, a processing unit may also be configured to cause the display device to display a virtual probe 908. The virtual probe 908 may be used to inspect any of the cardiac electrical signal features and/or the corresponding cardiac electrical signals that were sensed by a mapping probe. To do so, the processing unit may be configured to position the virtual probe 908 at one or more different positions on the cardiac map, in response to receiving a user input. That is, for example, the virtual probe 908 may be a cursor that a user may manipulate using an input device such as a mouse, a touchscreen, and/or the like.

In embodiments, as shown, the first portion 900 of the GUI may include a representation 910 of a selected region. As shown in FIGS. 9A-9E, the representation 910 of the selected region may be positioned adjacent the virtual probe 908 and may be repositioned by repositioning the virtual probe 908. In the illustrated embodiments, the selected region is represented by a conceptually circular shape 912, the interior 914 of which includes a perceptible alteration to the cardiac map. In the illustrative GUI depicted in FIGS. 9A-9E, the interior 914 of the representation 910 of the selected region is configured to emphasize the selected region by highlighting the portion of the cardiac map corresponding to the selected region. That is, as shown, the interior 914 of the representation 910 is rendered brighter than the rest of the cardiac map 904. In embodiments, the representation 910 may be configured according to any number of different techniques for emphasizing a portion of a cardiac map such as, for example, by using a different color palette, by changing other display parameters (e.g., contrast, sharpness, white-balance, filters, envelopes, etc.), by displaying a distinguished border, by displaying markers, and/or the like.

In embodiments, the processing unit may be configured to determine that the virtual probe 908 is positioned in a first position (e.g., with respect to the cardiac map); and to determine a selected region. The processing unit may determine that the virtual probe 908 is in a first position by detecting a cessation in a movement of the virtual probe 908 (e.g., by executing instructions from a user input device to cease movement of the virtual probe 908), and determining the position of the virtual probe 908. In some implementations, the processing unit may determine that the virtual probe 908 is positioned in the first position based on a combination of detecting cessation of movement of the virtual probe 908, determining the position of the virtual probe 908, and determining that the virtual probe 908 remained in the first position for a specified amount of time (e.g., a predetermined time threshold, a user-defined parameter, etc.).

The processing unit may determine the selected region based on the position and one or more selection parameters. For example, in embodiments, the selection region may be defined as a region having a certain radius surrounding the first position, where, in embodiments, the radius may be tracked using a technique that allows for taking into consideration the curvature of the surface of the cardiac map. In this manner, for example, the representation 910 of the selected region may be configured to appear as a flashlight beam illuminating the selected region of the cardiac map. In embodiments, the GUI may facilitate receiving user input to define, adjust, select, and/or otherwise manipulate one or more selection parameters. For example, embodiments may allow a user to change the radius of the flashlight beam incidence, to expand or contract the size of the selected region.

According to embodiments, in response to determining that the virtual probe 908 is positioned in the first position (and/or determining the selected region), the processing unit may automatically generate an activation waveform and/or activation histogram corresponding to the selected region, the representation 906 of which may be automatically presented in the second portion 902 of the GUI. In response to further user input, the processing unit may be configured to reposition the virtual probe 908 to a different position on the cardiac map. The processing unit may be configured to cause the display device to represent the portion of the activation waveform and/or activation histogram corresponding to the selection location. In embodiments, the processing unit may be configured to update the display of the representation 906 of the activation waveform and/or histogram continuously, continually, or on demand.

According to embodiments of the illustrative use case introduced above, it may be the case that some amount of breakthrough (i.e., a gap) from a first tissue region 916 to a second tissue region 918 is apparent based on evaluation of the cardiac map, review of some other tool, and/or a combination thereof, but it is not clear, from the cardiac map, where the breakthrough is occurring, and thus, the clinician may not be able to readily ascertain, from the map, an appropriate location to ablate to block the breakthrough. Using the regional review tool discussed above, the user may move the virtual probe 908 to different positions along the ablation line 920, and, as the virtual probe 908 is moved, the second portion 902 of the GUI is updated to present the representation 906, 922, 924, or 926, respectively corresponding to the position of the virtual probe 908 and the resulting selection region.

In this manner, for example, the user may be able to readily ascertain that, based on the clearly separated representations 930 and 932 of activations (e.g., having a flat signal in between them) of the representation 906 of the activation histogram corresponding to the selected region, the propagation is blocked within the selected region—that is, that the first activation 930 is not causing and/or affecting the second activation 932. Similarly, the user may be able to ascertain, based on the respective activations 934, 936, 938, 940, that there are no gaps within the selected regions depicted in FIGS. 9B and 9C. However, due to the presence of additional activity 942 between the activations 944 and 946 depicted in FIG. 9D, not excluded by the artifact rejection process during generation of the corresponding activation waveform, the user may readily ascertain there is a gap endpoint within the corresponding selected region, which may be contributing somewhat to the observed breakthrough. Similarly, the user may ascertain, based on the additional activity 948 between the activation 950 and 952 depicted in FIG. 9E, that there is a full breakthrough (gap) within the corresponding selected region. In this manner, the user may, more accurately and efficiently than with conventional systems, identify ablation targets.

Embodiments of the regional review tool described above may be useful for any number of situations and implementations. For example, embodiments may facilitate effective complex tachycardia analysis. Complex atrial tachycardia may result in a map that is difficult to interpret, and, in the case of ventricular tachycardia, bulk activation often hides channel potentials in the map annotations. Embodiments of the simplified, regional qualitative analysis facilitated by the regional review tool may mitigate these challenges. Additionally, or alternatively, embodiments may be useful for use cases involving detecting micro re-entry due to inherent challenges in locating areas of "wide-spanning activity," which could be ascertained readily using embodiments of the regional review tool. Embodiments of the regional review tool may be used for evaluating missing data and/or data associated with internal structures not depicted on the cardiac map. For example, embodiments may facilitate identify missing data by increasing the selection region radius and looking for flat areas in the activation waveform and/or histogram waveform. According to embodiments, any number of other use cases may be improved and/or available by implementing embodiments of the regional review tool described herein.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. For example, in embodiments, any number of different types of waveforms similar to the activation waveform, may be generated based on any number of different types of annotations (e.g., features extracted from electrical signals such as, e.g., EGMs). For example, embodiments may facilitate generation of annotation waveforms using any number of different aspects of embodiments of the methods described herein for generating activation waveforms. Illustrative examples of such waveforms include voltage waveforms, fractionation waveforms, velocity waveforms, and/or the like. Accordingly, the scope of the present disclosure is intended to embrace all such alternatives, modifications, and variations as fall within the scope of the claims, together with all equivalents thereof.

We claim:

1. A system for facilitating processing of cardiac information based on sensed electrical signals, the system comprising:
   a processing unit configured to:
      receive a set of electrical signals;
      receive an indication of a measurement location corresponding to each electrical signal of the set of electrical signals;
      generate an annotation waveform corresponding to the set of electrical signals, the annotation waveform based on deflections of the set of electrical signals from a baseline signal, wherein the baseline signal comprises at least one non-zero value and a deflection of the deflections from the baseline signal for the annotation waveform is from the non-zero value; and
      generate, based on the annotation waveform and a set of annotation mapping values, an annotation histogram.

2. The system of claim 1, wherein the processing unit is further configured to:
   generate, based on the set of electrical signals and corresponding locations, an electroanatomical cardiac map; and
   facilitate presentation, on a display device, of a graphical user interface (GUI) that includes the cardiac map and at least one of a representation of the annotation histogram.

3. The system of claim 2, wherein the annotation histogram represents a surface area of the cardiac map corresponding to certain annotation values.

4. The system of claim 3, wherein the processing unit is further configured to:

facilitate presentation, on the display device, of an interactive representation of a caliper;

receive, via a user input device, an indication of a user selection of a portion of the representation of the annotation histogram; and facilitate, based on the annotation histogram, presentation of a representation of an amount of surface area of the map corresponding to the selected portion of the annotation histogram.

5. The system of claim 4, wherein the representation of the amount of surface area of the map corresponding to the selected portion of the annotation histogram comprises at least one of a highlighted portion of the cardiac map and a numerical representation of the amount of surface area.

6. The system of claim 4, wherein the representation of the amount of surface area of the map corresponding to the selected portion of the annotated histogram comprises at least one of a representation of an absolute amount of surface area and a representation of a relative amount of surface area.

7. The system of claim 2, the GUI including the representation of the annotation histogram, wherein the representation of the annotation histogram comprises at least one of a discrete histogram and a continuous histogram, wherein a continuous histogram is represented as a displayed waveform.

8. The system of claim 7, wherein the processing unit determines whether to facilitate presentation of a representation of a discrete histogram or a continuous histogram based on number of values included in one or more of the bins of the annotation histogram.

9. The system of claim 2, the GUI further including a selection tool, and wherein the processor is configured to:
determine that the selection tool is positioned in a first position;
determine a selected region based on the first position and one or more selection parameters; and
generate the annotation waveform, the annotation waveform corresponding to a subset of the set of electrical signals associated with the selected region.

10. The system of claim 9, wherein the processing unit is further configured to facilitate presentation, in response to determining that the selection tool is positioned in the first position, of at least one of the representation of the annotation waveform and the representation of the annotation histogram.

11. The system of claim 1, wherein the annotation comprises at least one of activation, voltage, fractionation, and velocity.

12. A system of facilitating display of cardiac information, the system comprising:
a display device configured to present a representation of a cardiac map; and
a processing unit configured to:
receive a set of electrical signals;
receive an indication of a measurement location corresponding to each electrical signal of the set of electrical signals;
generate, based on the set of electrical signals, the cardiac map;
facilitate presentation, on the display device, of a graphical user interface (GUI) that includes the cardiac map and a virtual probe;
determine that the virtual probe is positioned in a first position;
determine a selected region based on the first position and one or more selection parameters; and
generate an annotation waveform, the annotation waveform corresponding to a subset of the set of electrical signals associated with the selected region, wherein the annotation waveform is based on deflections of the set of electrical signals from a baseline signal, wherein the baseline signal comprises at least one non-zero value and a deflection of the deflections from the baseline signal for the annotation waveform is from the non-zero value.

13. The system of claim 12, wherein the processing unit is further configured to facilitate presentation, in response to determining that the virtual probe is positioned in the first position, of at least one of the representation of the annotation waveform and a representation of an annotation histogram.

14. The system of claim 13, wherein the annotation comprises at least one of activation, voltage, fractionation, and velocity.

15. A method of facilitating processing of cardiac information, the method comprising:
receiving a set of electrical signals;
receiving an indication of a measurement location corresponding to each of the set of electrical signals;
generating an annotation waveform corresponding to the set of electrical signals, the annotation waveform based on deflections of the set of electrical signals from a baseline signal, wherein the baseline signal comprises at least one non-zero value and a deflection of the deflections from the baseline signal for the annotation waveform is from the non-zero value; and
generating, based on at least one of the annotation waveform and a set of annotation mapping values, an annotation histogram.

16. The method of claim 15, further comprising:
generating, based on the set of electrical signals and corresponding locations, an electroanatomical cardiac map of a cardiac structure; and
facilitating presentation, on a display device, of a graphical user interface (GUI) that includes the at least one of the cardiac map and a representation of the annotation histogram.

17. The method of claim 16, further comprising:
facilitating presentation, on the display device, of an interactive representation of a caliper;
receiving, via a user input device, an indication of a user selection of a portion of the representation of the annotation histogram; and
facilitating, based on the annotation histogram, presentation of a representation of an amount of surface area of the map corresponding to the selected portion of the annotation histogram.

18. The method of claim 17, wherein the representation of the amount of surface area of the map corresponding to the selected portion of the annotation histogram comprises at least one of a highlighted portion of the cardiac map and a numerical representation of the amount of surface area, the representation of the amount of surface area of the map corresponding to the selected portion of the annotated histogram comprising at least one of a representation of an absolute amount of surface area and a representation of a relative amount of surface area.

19. The method of claim 16, wherein the representation of the annotation histogram comprises at least one of a discrete histogram and a continuous histogram, wherein a continuous histogram is represented as a displayed waveform.

20. The method of claim 19, further comprising determining whether to facilitate presentation of a representation of a discrete histogram or a continuous histogram based on number of values included in one or more of the bins of the annotation histogram.

* * * * *